(12) United States Patent
Kumar et al.

(10) Patent No.: US 8,067,389 B2
(45) Date of Patent: Nov. 29, 2011

(54) SILENCING OF TGFβ TYPE II RECEPTOR EXPRESSION BY SIRNA

(75) Inventors: Nalin M. Kumar, Wilmette, IL (US); Beatrice Yue, Deerfield, IL (US); Shahid Siddiqui, Wilmette, IL (US); Asrar B. Malik, Hinsdale, IL (US); Jose S. Pulido, Rochester, MN (US)

(73) Assignee: The Broad of Trustees of the University of Illinois, Chicago, IL (US)

( * ) Notice: Subject to any disclaimer, the term of this patent is extended or adjusted under 35 U.S.C. 154(b) by 0 days.

(21) Appl. No.: 12/505,911

(22) Filed: Jul. 20, 2009

(65) Prior Publication Data

US 2009/0318537 A1 Dec. 24, 2009

Related U.S. Application Data

(63) Continuation of application No. 10/567,958, filed as application No. PCT/US2004/025984 on Aug. 10, 2004, now abandoned.

(60) Provisional application No. 60/495,161, filed on Aug. 13, 2003, provisional application No. 60/517,809, filed on Nov. 6, 2003, provisional application No. 60/561,542, filed on Apr. 9, 2004.

(51) Int. Cl.
| A61K 31/70 | (2006.01) |
| C07H 21/02 | (2006.01) |
| C07H 21/04 | (2006.01) |
| C12Q 1/68  | (2006.01) |
| C12N 5/00  | (2006.01) |

(52) U.S. Cl. ............... 514/44 A; 536/23.1; 536/24.1; 536/24.5; 435/375

(58) Field of Classification Search .................. None
See application file for complete search history.

(56) References Cited

U.S. PATENT DOCUMENTS

| 7,148,342 B2 | 12/2006 | Tolentino et al. |
| 7,345,027 B2 | 3/2008 | Tolentino et al. |
| 2003/0064944 A1 | 4/2003 | Murray et al. .......... 514/44 |
| 2004/0229266 A1 | 11/2004 | Tuschl et al. |
| 2005/0227936 A1 | 10/2005 | McSwiggen et al. |
| 2005/0287128 A1 | 12/2005 | Guerciolini et al. |
| 2007/0031844 A1* | 2/2007 | Khvorova et al. .......... 435/6 |

FOREIGN PATENT DOCUMENTS

| WO | WO 03/070197 A2 | 8/2003 |
| WO | WO 2005/031002 A2 | 4/2005 |

OTHER PUBLICATIONS

Vickers et al., The Journal of Biological Chemistry vol. 278(9):7108-7118, 2003.*
Arias et al., "Adenoviral Delivery of an Antisense RNA Complementary to the 3' Coding Sequence of Transforming Growth Factor-β1 Inhibits Fibrogenic Activities of Hepatic Stellate Cells[1]", Cell Growth & Differentiation 2002 13:265-273.
Cordeiro et al., Novel antisense oligonucleotides targeting TFG-β inhibit in vivo scarring and improve surgical outcome, Gene Therapy 2003 10:59-71.
Elbashir et al., "Duplexes of 21-nucleotide RNAs mediate RNA interference in cultured mammalian cells", Nature 2001 411:494-498.
Fire et al., "Potent and specific genetic interference by double-stranded RNA in Caenorhabditis elegans", Nature 1998 391:806-811.
Hannon, Gregory J., "RNA interference", Nature 2002 418:244-251.
Reich et al., "Small interfering RNA (siRNA) targeting VEGF effectively inhibits ocular neovascularization in a mouse model", Molecular Vision 2003 9:210-216.
Shen et al., "Specific inhibition of transforming growth factor-β2 expression in human osteoblast cells by antisense phosphorothioate oligonucleotides", Eur. J. Biochem. 2001 268:2331-2337.
Song et al., "RNA interference targeting Fas protects mice from fulminant hepatitis", Nature Medicine 2003 9(3):347-351.
Su et al., "Ribozyme to Human TGF-β1 mRNA Inhibits the Proliferation of Human Vascular Smooth Muscle Cells", Biochemical and Biophysical Research Communications 2000 278:401-407.
Yamamoto et al., "Ribozyme Oligonucleotides Against Transforming Growth Factor-β Inhibited Neointimal Formation After Vascular Injury in Rat Model", Circulation 2000 102:1308-1314.
NCBI Genbank Accession M85079 [gi:339569] Jul. 31, 1992-Jan. 14, 1995 with Revision History.
Iyer et al., "Targeting TGFβ Signaling for Cancer therapy", Cancer Biology &Therapy 2005 4:3, 261-266.
Lin et al ., "Expression Cloning of the TGF-β Type II Receptor, a Functional Transmembrane Serine/Threonine Kinase", Cell 1992 68:775-785.
Tuschl et al., "Selection of siRNA duplexes from the target mRNA sequence", The siRNA user guide Apr. 16, 2003, 6 pages.
Caplen et al. "Specific Inhibition of Gene Expression by Small Double-Stranded RNAs in Invertebrate and Vertebrate Systems", Proceedings of the National Academy of Science 2001 vol. 98(17): 9742-9747.
Nakamura et al. "RNA Interference Targeting Transforming Growth Factor-β Type II Receptor Suppresses Ocular Inflammation and Fibrosis", Molecular Vision 2004 vol. 10: 703-711.
Search Report from Corresponding EPO Application No. 04780766.4, Jun. 1, 2010.

* cited by examiner

Primary Examiner — Sean McGarry
(74) Attorney, Agent, or Firm — Licata & Tyrrell, P.C.

(57) ABSTRACT

The present application is directed to siRNA-based silencing of the type II receptor of TGFβ. siRNAs that target this receptor abrogate the receptor protein and transcript, TGFβ-mediated processes such as fibronectin assembly and cell migration also are inhibited and the molecules of the invention are efficacious in reducing the inflammatory response and matrix deposition. These findings show that siRNAs can be successfully delivered both in vitro and in vivo to regulate the TGFβ type II receptor level and modulate wound response. Methods and compositions exploiting the findings of the present invention have a wide-ranging application, extending from treatment of disorders of the eye to other organs and tissues throughout the body.

13 Claims, 9 Drawing Sheets

INHIBITION OF TβTII EXPRESSION BY RNAi

SUPPRESSION OF TGFβRII EXPRESSION BY siRNA

Target Sequence 1: AAGTCGGTTAATAACGACATG (SEQ ID NO: 13)
Position in Gene Sequence: 423
GC Content:38.1%
Sense Strand siRNA: GUCGGUUAAUAACGACAUGtt (SEQ ID NO: 14)
Antisense Strand siRNA: CAUGUCGUUAUUAACCGACtt (SEQ ID NO:15)

Target Sequence 2: AACGACATGATAGTCACTGAC (SEQ ID NO: 16)
Position in Gene Sequence: 435
GC Content: 42.9%
Sense Strand siRNA: CGACAUGAUAGUCACUGACtt (SEQ ID NO: 17)
Antisense Strand siRNA: GUCAGUGACUAUCAUGUCGtt (SEQ ID NO:18)

Target Sequence 3: AACAACGGTGCAGTCAAGTTT (SEQ ID NO: 19)
Position in Gene Sequence: 456
GC Content: 42.9%
Sense Strand siRNA: CAACGGUGCAGUCAAGUUUtt (SEQ ID NO: 20)
Antisense Strand siRNA: AAACUUGACUGCACCGUUGtt (SEQ ID NO:21)

Target Sequence 4: AACGGTGCAGTCAAGTTTCCA (SEQ ID NO: 22)
Position in Gene Sequence: 459
GC Content: 47.6%
Sense Strand siRNA: CGGUGCAGUCAAGUUUCCAtt (SEQ ID NO: 23)
Antisense Strand siRNA: UGGAAACUUGACUGCACCGtt (SEQ ID NO:21)

Target Sequence 5: AAGTTTCCACAACTGTGTAAA (SEQ ID NO: 25)
Position in Gene Sequence: 471
GC Content: 33.3%
Sense Strand siRNA: GUUUCCACAACUGUGUAAAtt (SEQ ID NO: 26)
Antisense Strand siRNA: UUUACACAGUUGUGGAAACtt (SEQ ID NO:27)

Target Sequence 6: AAATCCTGCATGAGCAACTGC (SEQ ID NO: 28)
Position in Gene Sequence: 528
GC Content: 47.6%
Sense Strand siRNA: AUCCUGCAUGAGCAACUGCtt (SEQ ID NO: 29)
Antisense Strand siRNA: GCAGUUGCUCAUGCAGGAUtt (SEQ ID NO:30)

Target Sequence 7: AAGTCTGTGTGGCTGTATGGA (SEQ ID NO: 31)
Position in Gene Sequence: 580
GC Content: 47.6%
Sense Strand siRNA: GUCUGUGUGGCUGUAUGGAtt (SEQ ID NO: 32)
Antisense Strand siRNA: UCCAUACAGCCACACAGACtt (SEQ ID NO:33)

Target Sequence 8: AAAGAATGACGAGAACATAAC (SEQ ID NO: 34)
Position in Gene Sequence: 602
GC Content: 33.3%
Sense Strand siRNA: AGAAUGACGAGAACAUAACtt (SEQ ID NO: 35)
Antisense Strand siRNA: GUUAUGUUCUCGUCAUUCUtt (SEQ ID NO:36)

*FIG. 3A*

Target Sequence 9: AATGACGAGAACATAACACTA (SEQ ID NO: 37)
Position in Gene Sequence: 606
GC Content:33.3%
Sense Strand siRNA: UGACGAGAACAUAACACUAtt (SEQ ID NO: 38)
Antisense Strand siRNA: UAGUGUUAUGUUCUCGUCAtt (SEQ ID NO:39)

Target Sequence 10: AACATAACACTAGAGACAGTT (SEQ ID NO: 40)
Position in Gene Sequence: 615
GC Content: 33.3%
Sense Strand siRNA: CAUAACACUAGAGACAGUUtt (SEQ ID NO: 41)
Antisense Strand siRNA: AACUGUCUCUAGUGUUAUGtt (SEQ ID NO:42)

Target Sequence 11: AACACTAGAGACAGTTTGCCA (SEQ ID NO: 43)
Position in Gene Sequence: 620
GC Content: 42.9%
Sense Strand siRNA: CACUAGAGACAGUUGCCAtt (SEQ ID NO: 44)
Antisense Strand siRNA: UGGCAAACUGUCUCUAGUGtt (SEQ ID NO: 45)

Target Sequence 12: AAGATGCTGCTTCTCCAAAGT (SEQ ID NO: 46)
Position in Gene Sequence: 676
GC Content: 42.9%
Sense Strand siRNA: GAUGCUGCUUCUCCAAAGUtt (SEQ ID NO: 47)
Antisense Strand siRNA: ACUUUGGAGAAGCAGCAUCtt (SEQ ID NO:48)

Target Sequence 13: AAGCCTGGTGAGACTTTCTTC (SEQ ID NO: 49)
Position in Gene Sequence: 717
GC Content: 47.6%
Sense Strand siRNA: GCCUGGUGAGACUUUCUUCtt (SEQ ID NO: 50)
Antisense Strand siRNA: GAAGAAAGUCUCACCAGGCtt (SEQ ID NO:51)

Target Sequence 14: AATGACAACATCATCTTCTCA (SEQ ID NO: 52)
Position in Gene Sequence: 765
GC Content: 33.3%
Sense Strand siRNA: UGACAACAUCAUCUUCUCAtt (SEQ ID NO: 53)
Antisense Strand siRNA: UGAGAAGAUGAUGUUGUCAtt (SEQ ID NO:54)

Target Sequence 15: AACATCATCTTCTCAGAAGAA (SEQ ID NO: 55)
Position in Gene Sequence: 771
GC Content: 33.3%
Sense Strand siRNA: CAUCAUCUUCUCAGAAGAAtt (SEQ ID NO: 56)
Antisense Strand siRNA: UUCUUCUGAGAAGAUGAUGtt (SEQ ID NO:57)

*FIG. 3B*

Target Sequence 16: AAGAATATAACACCAGCAATC (SEQ ID NO: 157)
Position in Gene Sequence: 787
GC Content:33.3%
Sense Strand siRNA: GAAUAUAACACCAGCAAUCtt (SEQ ID NO: 58)
Antisense Strand siRNA: GAUUGCUGGUGUUAUAUUCtt (SEQ ID NO:59)

Target Sequence 17: AATATAACACCAGCAATCCTG (SEQ ID NO: 60)
Position in Gene Sequence: 790
GC Content: 38.1%
Sense Strand siRNA: UAUAACACCAGCAAUCCUGtt (SEQ ID NO: 61)
Antisense Strand siRNA: CAGGAUUGCUGGUGUUAUAtt (SEQ ID NO:62)

Target Sequence 18: AACACCAGCAATCCTGACTTG (SEQ ID NO: 63)
Position in Gene Sequence: 795
GC Content: 47.6%
Sense Strand siRNA: CACCAGCAAUCCUGACUUGtt (SEQ ID NO: 64)
Antisense Strand siRNA: CAAGUCAGGAUUGCUGGUGtt (SEQ ID NO: 65)

Target Sequence 19: AATCCTGACTTGTTGCTAGTC (SEQ ID NO: 66)
Position in Gene Sequence: 804
GC Content: 42.9%
Sense Strand siRNA: UCCUGACUUGUUGCUAGUCtt (SEQ ID NO: 67)
Antisense Strand siRNA: GACUAGCAACAAGUCAGGAtt (SEQ ID NO:68)

Target Sequence 20: AAGCTGAGTTCAACCTGGAA (SEQ ID NO: 69)
Position in Gene Sequence: 921
GC Content: 47.6%
Sense Strand siRNA: GCUGAGUUCAACCUGGGAAtt (SEQ ID NO: 70)
Antisense Strand siRNA: UUCCCAGGUUGAACUCAGCtt (SEQ ID NO:71)

Target Sequence 21: AAGATGACCGCTCTGACATCA (SEQ ID NO: 72)
Position in Gene Sequence: 997
GC Content: 47.6%
Sense Strand siRNA: GAUGACCGCUCUGACAUCAtt (SEQ ID NO: 73)
Antisense Strand siRNA: UGAUGUCAGAGCGGUCAUCtt (SEQ ID NO:74)

Target Sequence 22: AACAACATCAACCACAACACA (SEQ ID NO: 75)
Position in Gene Sequence: 1032
GC Content: 38.1%
Sense Strand siRNA: CAACAUCAACCACAACACAtt (SEQ ID NO: 76)
Antisense Strand siRNA: UGUGUUGUGGUUGAUGUUGtt (SEQ ID NO:77)

*FIG. 3C*

Target Sequence 23: AACATCAACCACAACACAGAG (SEQ ID NO: 78)
Position in Gene Sequence: 1035
GC Content:42.9%
Sense Strand siRNA: CAUCAACCACAACACAGAGtt (SEQ ID NO: 79)
Antisense Strand siRNA: CUCUGUGUUGUGGUUGAUGtt (SEQ ID NO:80)

Target Sequence 24: AAGCTGAAGCAGAACACTTCA (SEQ ID NO: 81)
Position in Gene Sequence: 1119
GC Content: 42.9%
Sense Strand siRNA: GCUGAAGCAGAACACUUAtt (SEQ ID NO: 81)
Antisense Strand siRNA: UGAAGUGUUCUGCUUCAGCtt (SEQ ID NO:82)

Target Sequence 25: AAGCAGAACACTTCAGAGCAG (SEQ ID NO: 83)
Position in Gene Sequence: 1125
GC Content: 47.6%
Sense Strand siRNA: GCAGAACACUUCAGAGCAGtt (SEQ ID NO: 84)
Antisense Strand siRNA: CUGCUCUGAAGUGUUCUGCtt (SEQ ID NO: 85)

Target Sequence 26: AACACTTCAGAGCAGTTTGAG (SEQ ID NO: 86)
Position in Gene Sequence: 1131
GC Content: 42.9%
Sense Strand siRNA: CACUUCAGAGCAGUUUGAGtt (SEQ ID NO: 87)
Antisense Strand siRNA: CUCAAACUGCUCUGAAGUGtt (SEQ ID NO:88)

Target Sequence 27: AAGATCTTTCCCTATGAGGAG (SEQ ID NO: 89)
Position in Gene Sequence: 1164
GC Content: 42.9%
Sense Strand siRNA: GAUCUUUCCCUAUGAGGAGtt (SEQ ID NO: 90)
Antisense Strand siRNA: CUCCUCAUAGGGAAAGAUCtt (SEQ ID NO:91)

Target Sequence 28: AAGACAGAGAAGGACATCTTC (SEQ ID NO: 92)
Position in Gene Sequence: 1197
GC Content: 42.9%
Sense Strand siRNA: GACAGAGAAGGACAUCUUCtt (SEQ ID NO: 93)
Antisense Strand siRNA: GAAGAUGUCCUUCUCUGUCtt (SEQ ID NO:94)

Target Sequence 29: AAGGACATCTTCTCAGACATC (SEQ ID NO: 95)
Position in Gene Sequence: 1206
GC Content: 42.9%
Sense Strand siRNA: GGACAUCUUCUCAGACAUCtt (SEQ ID NO: 96)
Antisense Strand siRNA: GAUGUCUGAGAAGAUGUCCtt (SEQ ID NO:97)

FIG. 3D

Target Sequence 30: AATCTGAAGCATGAGAACATA (SEQ ID NO: 98)
Position in Gene Sequence: 1227
GC Content: 33.3%
Sense Strand siRNA: UCUGAAGCAUGAGAACAUAtt (SEQ ID NO: 99)
Antisense Strand siRNA: UAUGUUCUCAUGCUUCAGAtt (SEQ ID NO:100)

Target Sequence 31: AAGCATGAGAACATACTCCAG (SEQ ID NO: 158)
Position in Gene Sequence: 1233
GC Content: 42.9%
Sense Strand siRNA: GCAUGAGAACAUACUCCAGtt (SEQ ID NO: 101)
Antisense Strand siRNA: CUGGAGUAUGUUCUCAUGCtt (SEQ ID NO:102)

Target Sequence 32: AACATACTCCAGTTCCTGACG (SEQ ID NO: 103)
Position in Gene Sequence: 1242
GC Content: 47.6%
Sense Strand siRNA: CAUACUCCAGUUCCUGACGtt (SEQ ID NO: 104)
Antisense Strand siRNA: CGUCAGGAACUGGAGUAUGtt (SEQ ID NO: 105)

Target Sequence 33: AAGACGGAGTTGGGGAAACAA (SEQ ID NO: 106)
Position in Gene Sequence: 1275
GC Content: 47.6%
Sense Strand siRNA: GACGGAGUUGGGGAAACAAtt (SEQ ID NO: 107)
Antisense Strand siRNA: UUGUUUCCCCAACUCCGUCtt (SEQ ID NO:108)

Target Sequence 34: AAACAATACTGGCTGATCACC (SEQ ID NO: 109)
Position in Gene Sequence: 1290
GC Content: 42.9%
Sense Strand siRNA: ACAAUACUGGCUGAUCACCtt (SEQ ID NO: 110)
Antisense Strand siRNA: GGUGAUCAGCCAGUAUUGUtt (SEQ ID NO:111)

Target Sequence 35: AAGAGCTCCAATATCCTCGTG (SEQ ID NO: 112)
Position in Gene Sequence: 1476
GC Content: 47.6%
Sense Strand siRNA: GAGCUCCAAUAUCCUCGUGtt (SEQ ID NO: 113)
Antisense Strand siRNA: CACGAGGAUAUUGGAGCUCtt (SEQ ID NO:114)

Target Sequence 36: AATATCCTCGTGAAGAACGAC (SEQ ID NO: 115)
Position in Gene Sequence: 1485
GC Content: 42.9%
Sense Strand siRNA: UAUCCUCGUGAAGAACGACtt (SEQ ID NO: 116)
Antisense Strand siRNA: GUCGUUCUUCACGAGGAUAtt (SEQ ID NO:117)

*FIG. 3E*

Target Sequence 37: AACTGCAAGATACATGGCTCC (SEQ ID NO: 118)
Position in Gene Sequence: 1595
GC Content: 47.6%
Sense Strand siRNA: CUGCAAGAUACAUGGCUCCtt (SEQ ID NO: 119)
Antisense Strand siRNA: GGAGCCAUGUAUCUUGCAGtt (SEQ ID NO:120)

Target Sequence 38: AAGATACATGGCTCCAGAAGT (SEQ ID NO: 121)
Position in Gene Sequence: 1601
GC Content: 42.9%
Sense Strand siRNA: GAUACAUGGCUCCAGAAGUtt (SEQ ID NO: 122)
Antisense Strand siRNA: ACUUCUGGAGCCAUGUAUCtt (SEQ ID NO:123)

Target Sequence 39: AAGTCCTAGAATCCAGGATGA (SEQ ID NO: 124)
Position in Gene Sequence: 1618
GC Content: 42.9%
Sense Strand siRNA: GUCCUAGAAUCCAGGAUGAtt (SEQ ID NO: 125)
Antisense Strand siRNA: UCAUCCUGGAUUCUAGGACtt (SEQ ID NO: 126)

Target Sequence 40: AATCCAGGATGAATTTGGAGA (SEQ ID NO: 127)
Position in Gene Sequence: 1627
GC Content: 38.1%
Sense Strand siRNA: UCCAGGAUGAAUUUGGAGAtt (SEQ ID NO: 128)
Antisense Strand siRNA: UCUCCAAAUUCAUCCUGGAtt (SEQ ID NO:129)

Target Sequence 41: AATTTGGAGAATGCTGAGTCC (SEQ ID NO: 130)
Position in Gene Sequence: 1638
GC Content: 42.9%
Sense Strand siRNA: UUUGGAGAAUGCUGAGUCCtt (SEQ ID NO: 131)
Antisense Strand siRNA: GGACUCAGCAUUCUCCAAAtt (SEQ ID NO:132)

Target Sequence 42: AATGCTGAGTCCTTCAAGCAG (SEQ ID NO: 133)
Position in Gene Sequence: 1647
GC Content: 47.6%
Sense Strand siRNA: UGCUGAGUCCUUCAAGCAGtt (SEQ ID NO: 134)
Antisense Strand siRNA: CUGCUUGAAGGACUCAGCAtt (SEQ ID NO:135)

Target Sequence 43: AAATGACATCTCGCTGTAATG (SEQ ID NO: 136)
Position in Gene Sequence: 1702
GC Content: 38.1%
Sense Strand siRNA: AUGACAUCUCGCUGUAAUGtt (SEQ ID NO: 137)
Antisense Strand siRNA: CAUUACAGCGAGAUGUCAUtt (SEQ ID NO:138)

*FIG. 3F*

Target Sequence 44: AATGCAGTGGGAGAAGTAAAA (SEQ ID NO: 139)
Position in Gene Sequence: 1719
GC Content: 38.1%
Sense Strand siRNA: UGCAGUGGGAGAAGUAAAAtt (SEQ ID NO: 140)
Antisense Strand siRNA: UUUUACUUCUCCCACUGCAtt (SEQ ID NO:141)

Target Sequence 45: AAGATTATGAGCCTCCATTTG (SEQ ID NO: 142)
Position in Gene Sequence: 1738
GC Content: 38.1%
Sense Strand siRNA: GAUUAUGAGCCUCCAUUUGtt (SEQ ID NO: 143)
Antisense Strand siRNA: CAAAUGGAGGCUCAUAAUCtt (SEQ ID NO:144)

Target Sequence 46: AAAGCATGAAGGACAACGTGT (SEQ ID NO: 145)
Position in Gene Sequence: 1789
GC Content: 42.9%
Sense Strand siRNA: AGCAUGAAGGACAACGUGUtt (SEQ ID NO: 146)
Antisense Strand siRNA: ACACGUUGUCCUUCAUGCUtt (SEQ ID NO: 147)

Target Sequence 47: AAGGACAACGTGTTGAGAGAT (SEQ ID NO: 148)
Position in Gene Sequence: 1797
GC Content: 42.9%
Sense Strand siRNA: GGACAACGUGUUGAGAGAUtt (SEQ ID NO: 149)
Antisense Strand siRNA: AUCUCUCAACACGUUGUCCtt (SEQ ID NO:150)

Target Sequence 48: AAATTCCCAGCTTCTGGGTCA (SEQ ID NO: 151)
Position in Gene Sequence: 1831
GC Content: 47.6%
Sense Strand siRNA: AUUCCCAGCUUCUGGCUCAtt (SEQ ID NO: 152)
Antisense Strand siRNA: UGAGCCAGAAGCUGGGAAUtt (SEQ ID NO:153)

Target Sequence 49: AAGACGGCTCCCTAAACACTA (SEQ ID NO: 154)
Position in Gene Sequence: 2011
GC Content: 47.6%
Sense Strand siRNA: GACGGCUCCCUAAACACUAtt (SEQ ID NO: 155)
Antisense Strand siRNA: UAGUGUUUAGGGAGCCGUCtt (SEQ ID NO:156)

FIG. 3G

TβRII  DAPI
A 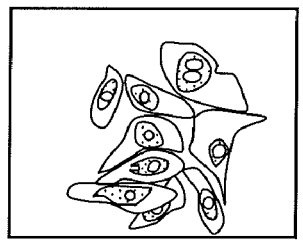 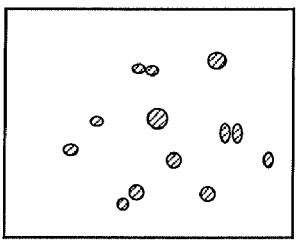 E
B 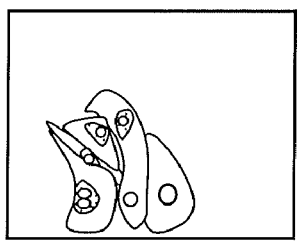 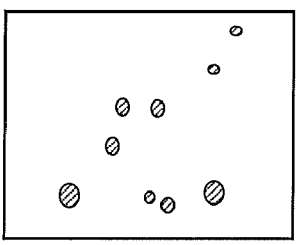 F
C 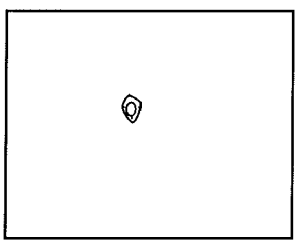 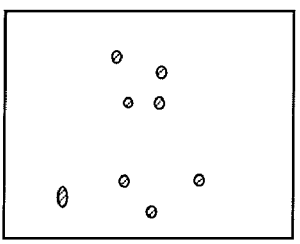 G
D 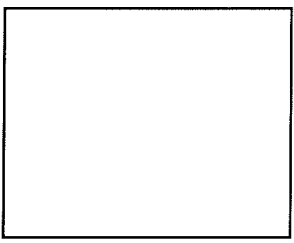 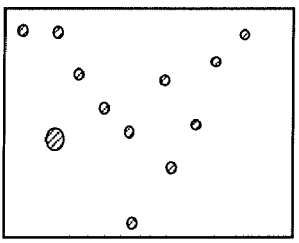 H
FIG. 4

```
                        SEQUENCE LISTING

<160> NUMBER OF SEQ ID NOS: 161

<210> SEQ ID NO 1
<211> LENGTH: 21
<212> TYPE: DNA
<213> ORGANISM: Homo sapiens

<400> SEQUENCE: 1
aatcctgcat gagcaactgc a                                               21

<210> SEQ ID NO 2
<211> LENGTH: 21
<212> TYPE: DNA
<213> ORGANISM: Homo sapiens

<400> SEQUENCE: 2
aaggccaagc tgaagcagaa c                                               21

<210> SEQ ID NO 3
<211> LENGTH: 20
<212> TYPE: DNA
<213> ORGANISM: Homo sapiens

<400> SEQUENCE: 3
agcatgagaa catactccag                                                 20

<210> SEQ ID NO 4
<211> LENGTH: 21
<212> TYPE: DNA
<213> ORGANISM: Homo sapiens

<400> SEQUENCE: 4
aagacgcgga agctcatgga g                                               21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
```

-continued uccugcauga gcaacugcat t  21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
ttaggacgua cucguugacg u  21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 7
ggccaagcug aagcagaact t  21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
ttccgguucg acuucgucuu g  21

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 9
gcaugagaac auacuccagt t  21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
ttcguacucu uguaugaggu c  21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gacgcggaag cucauggagt t  21

<210> SEQ ID NO 12
<211> LENGTH: 21
<212> TYPE: DNA
<213> ORGANISM: Artificial Sequence
<220> FEATURE:

-continued

<223> OTHER INFORMATION: Synthetic oligonucleotide

<400> SEQUENCE: 12
ttcugcgccu ucgaguaccu c                                              21

<210> SEQ ID NO 13
<211> LENGTH: 21
<212> TYPE: DNA
<213> ORGANISM: Homo sapiens

<400> SEQUENCE: 13
aagtcggtta ataacgacat g                                              21

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
gucguuaaua acgacaugtt                                                20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 15
caugucguua uuaaccgact t                                              21

<210> SEQ ID NO 16
<211> LENGTH: 21
<212> TYPE: DNA
<213> ORGANISM: Homo sapiens

<400> SEQUENCE: 16
aacgacatga tagtcactga c                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 17
cgacaugaua gucacugact t                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
gucagugacu aucaugucgt t                                              21

<210> SEQ ID NO 19
<211> LENGTH: 21
<212> TYPE: DNA
<213> ORGANISM: Homo sapiens

```
<400> SEQUENCE: 19
aacaacggtg cagtcaagtt t                                              21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
caacggugca gucaaguuut t                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 21
aaacuugacu gcaccguugt t                                              21

<210> SEQ ID NO 22
<211> LENGTH: 21
<212> TYPE: DNA
<213> ORGANISM: Homo sapiens

<400> SEQUENCE: 22
aacggtgcag tcaagtttcc a                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
cggugcaguc aaguuuccat t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
uggaaacuug acugcaccgt t                                              21

<210> SEQ ID NO 25
<211> LENGTH: 21
<212> TYPE: DNA
<213> ORGANISM: Homo sapiens

<400> SEQUENCE: 25
aagtttccac aactgtgtaa a                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 26
guuuccacaa cuguguaaat t                                              21

<210> SEQ ID NO 27
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 27
uuuacacagu uguggaaact t                                              21

<210> SEQ ID NO 28
<211> LENGTH: 21
<212> TYPE: DNA
<213> ORGANISM: Homo sapiens

<400> SEQUENCE: 28
aaatcctgca tgagcaactg c                                              21

<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 29
auccugcaug agcaacugct t                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
gcaguugcuc augcaggaut t                                              21

<210> SEQ ID NO 31
<211> LENGTH: 21
<212> TYPE: DNA
<213> ORGANISM: Homo sapiens

<400> SEQUENCE: 31
aagtctgtgt ggctgtatgg a                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
gucugugugg cuguauggat t                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 33
uccauacagc cacacagact t                                              21

<210> SEQ ID NO 34
<211> LENGTH: 21
<212> TYPE: DNA
<213> ORGANISM: Homo sapiens

<400> SEQUENCE: 34
aaagaatgac gagaacataa c                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35
agaaugacga gaacauaact t                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
guuauguucu cgucauucut t                                              21

<210> SEQ ID NO 37
<211> LENGTH: 21
<212> TYPE: DNA
<213> ORGANISM: Homo sapiens

<400> SEQUENCE: 37
aatgacgaga acataacact a                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
ugacgagaac auaacacuat t                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
uaguguuaug uucucgucat t                                              21

<210> SEQ ID NO 40
<211> LENGTH: 21
<212> TYPE: DNA
<213> ORGANISM: Homo sapiens

<400> SEQUENCE: 40
```

-continued aacataacac tagagacagt t                                          21

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41
cauaacacua gagacaguut t                                          21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 42
aacugucucu aguguuaugt t                                          21

<210> SEQ ID NO 43
<211> LENGTH: 21
<212> TYPE: DNA
<213> ORGANISM: Homo sapiens

<400> SEQUENCE: 43
aacactagag acagtttgcc a                                          21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44
cacuagagac aguuugccat t                                          21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 45
uggcaaacug ucucuacugt t                                          21

<210> SEQ ID NO 46
<211> LENGTH: 21
<212> TYPE: DNA
<213> ORGANISM: Homo sapiens

<400> SEQUENCE: 46
aagatgctgc ttctccaaag t                                          21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 47

```
gaugcugcuu cuccaaagut t                                              21
```

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 48

```
acuuuggaga agcagcauct t                                              21
```

<210> SEQ ID NO 49
<211> LENGTH: 21
<212> TYPE: DNA
<213> ORGANISM: Homo sapiens

<400> SEQUENCE: 49

```
aagcctggtg agactttctt c                                              21
```

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50

```
gccuggugag acuuucuuct t                                              21
```

<210> SEQ ID NO 51
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 51

```
gaagaaaguc ucaccaggct t                                              21
```

<210> SEQ ID NO 52
<211> LENGTH: 21
<212> TYPE: DNA
<213> ORGANISM: Homo sapiens

<400> SEQUENCE: 52

```
aatgacaaca tcatcttctc a                                              21
```

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53

```
ugacaacauc aucuucucat t                                              21
```

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 54

-continued

```
ugagaagaug auguugucat t                                              21

<210> SEQ ID NO 55
<211> LENGTH: 21
<212> TYPE: DNA
<213> ORGANISM: Homo sapiens

<400> SEQUENCE: 55
aacatcatct tctcagaaga a                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 56
caucaucuuc ucagaagaat t                                              21

<210> SEQ ID NO 57
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 57
uucuucugag aagaugaugt t                                              21

<210> SEQ ID NO 58
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 58
gaauauaaca ccagcaauct t                                              21

<210> SEQ ID NO 59
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 59
gauugcuggu guuauauuct t                                              21

<210> SEQ ID NO 60
<211> LENGTH: 21
<212> TYPE: DNA
<213> ORGANISM: Homo sapiens

<400> SEQUENCE: 60
aatataacac cagcaatcct g                                              21

<210> SEQ ID NO 61
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 61
```
uauaacacca gcaauccugt t        21

<210> SEQ ID NO 62
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 62
caggauugcu gguguuauat t        21

<210> SEQ ID NO 63
<211> LENGTH: 21
<212> TYPE: DNA
<213> ORGANISM: Homo sapiens

<400> SEQUENCE: 63
aacaccagca atcctgactt g        21

<210> SEQ ID NO 64
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 64
caccagcaau ccugacuugt t        21

<210> SEQ ID NO 65
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 65
caagucagga uugcuggugt t        21

<210> SEQ ID NO 66
<211> LENGTH: 21
<212> TYPE: DNA
<213> ORGANISM: Homo sapiens

<400> SEQUENCE: 66
aatcctgact tgttgctagt c        21

<210> SEQ ID NO 67
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 67
uccugacuug uugcuaguct t        21

<210> SEQ ID NO 68
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 68
gacuagcaac aagucaggat t                                    21

<210> SEQ ID NO 69
<211> LENGTH: 21
<212> TYPE: DNA
<213> ORGANISM: Homo sapiens

<400> SEQUENCE: 69
aagctgagtt caacctggga a                                    21

<210> SEQ ID NO 70
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 70
gcugaguuca accugggaat t                                    21

<210> SEQ ID NO 71
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 71
uucccagguu gaacucagct t                                    21

<210> SEQ ID NO 72
<211> LENGTH: 21
<212> TYPE: DNA
<213> ORGANISM: Homo sapiens

<400> SEQUENCE: 72
aagatcaccg ctctgacatc a                                    21

<210> SEQ ID NO 73
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 73
gaugaccgcu cugacaucat t                                    21

<210> SEQ ID NO 74
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 74
ugaugucaga gcggucauct t                                    21

<210> SEQ ID NO 75
<211> LENGTH: 21
<212> TYPE: DNA
<213> ORGANISM: Homo sapiens

<400> SEQUENCE: 75
aacaacatca accacaacac a                                    21

```
<210> SEQ ID NO 76
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 76
caacaucaac cacaacacat t                                              21

<210> SEQ ID NO 77
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 77
uguguugugg uugauguugt t                                              21

<210> SEQ ID NO 78
<211> LENGTH: 21
<212> TYPE: DNA
<213> ORGANISM: Homo sapiens

<400> SEQUENCE: 78
aacatcaacc acaacacaga g                                              21

<210> SEQ ID NO 79
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 79
caucaaccac aacacagagt t                                              21

<210> SEQ ID NO 80
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 80
cucuguguug ugguugaugt t                                              21

<210> SEQ ID NO 81
<211> LENGTH: 21
<212> TYPE: DNA
<213> ORGANISM: Homo sapiens

<400> SEQUENCE: 81
aagctgaagc agaacacttc a                                              21

<210> SEQ ID NO 82
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 82
ugaaguguuc ugcuucagct t                                              21
```

```
<210> SEQ ID NO 83
<211> LENGTH: 21
<212> TYPE: DNA
<213> ORGANISM: Homo sapiens

<400> SEQUENCE: 83
aagcagaaca cttcagagca g                                            21

<210> SEQ ID NO 84
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 84
gcagaacacu ucagagcagt t                                            21

<210> SEQ ID NO 85
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 85
cugcucugaa guguucugct t                                            21

<210> SEQ ID NO 86
<211> LENGTH: 21
<212> TYPE: DNA
<213> ORGANISM: Homo sapiens

<400> SEQUENCE: 86
aacacttcag agcagtttga g                                            21

<210> SEQ ID NO 87
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 87
cacuucagag cacuuugagt t                                            21

<210> SEQ ID NO 88
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 88
cucaaacugc ucugaagugt t                                            21

<210> SEQ ID NO 89
<211> LENGTH: 21
<212> TYPE: DNA
<213> ORGANISM: Homo sapiens

<400> SEQUENCE: 89
aagatctttc cctatgagga g                                            21

<210> SEQ ID NO 90
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 90
gaucuucccc uaugaggagt t                                              21

<210> SEQ ID NO 91
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 91
cuccucauag ggaaagauct t                                              21

<210> SEQ ID NO 92
<211> LENGTH: 21
<212> TYPE: DNA
<213> ORGANISM: Homo sapiens

<400> SEQUENCE: 92
aagacagaga aggacatctt c                                              21

<210> SEQ ID NO 93
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 93
gacagagaag gacaucuuct t                                              21

<210> SEQ ID NO 94
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 94
gaagaugucc uucucuguct t                                              21

<210> SEQ ID NO 95
<211> LENGTH: 21
<212> TYPE: DNA
<213> ORGANISM: Homo sapiens

<400> SEQUENCE: 95
aaggacatct tctcagacat c                                              21

<210> SEQ ID NO 96
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 96
ggacaucuuc ucagacauct t                                              21

<210> SEQ ID NO 97
```

-continued

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 97
gaugucugag aagaugucct t                                            21

<210> SEQ ID NO 98
<211> LENGTH: 21
<212> TYPE: DNA
<213> ORGANISM: Homo sapiens

<400> SEQUENCE: 98
attctgaagc atgagaacat a                                            21

<210> SEQ ID NO 99
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 99
ucugaagcau gagaacauat t                                            21

<210> SEQ ID NO 100
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 100
uauguucuca ugcuucagat t                                            21

<210> SEQ ID NO 101
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 101
gcaugagaac auacuccagt t                                            21

<210> SEQ ID NO 102
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 102
cuggaguaug uucucaugct t                                            21

<210> SEQ ID NO 103
<211> LENGTH: 21
<212> TYPE: DNA
<213> ORGANISM: Homo sapiens

<400> SEQUENCE: 103
aacatactcc agttcctgac g                                            21

<210> SEQ ID NO 104
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 104
cauacuccag uuccugacgt t                                                   21

<210> SEQ ID NO 105
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 105
cgucaggaac uggaguaugt t                                                   21

<210> SEQ ID NO 106
<211> LENGTH: 21
<212> TYPE: DNA
<213> ORGANISM: Homo sapiens

<400> SEQUENCE: 106
aagacggagt tggggaaaca a                                                   21

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 107
gacggaguug gggaaacaat t                                                   21

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 108
uuguuccccc aacuccguct t                                                   21

<210> SEQ ID NO 109
<211> LENGTH: 21
<212> TYPE: DNA
<213> ORGANISM: Homo sapiens

<400> SEQUENCE: 109
aaacaatact ggctgatcac c                                                   21

<210> SEQ ID NO 110
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 110
acaauacugg cugaucacct t                                                   21

<210> SEQ ID NO 111
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 111
ggugaucagc caguauugut t                                            21

<210> SEQ ID NO 112
<211> LENGTH: 21
<212> TYPE: DNA
<213> ORGANISM: Homo sapiens

<400> SEQUENCE: 112
aagagctcca atatcctcgt g                                            21

<210> SEQ ID NO 113
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 113
gagcuccaau auccucgugt t                                            21

<210> SEQ ID NO 114
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 114
cacgaggaua uuggagcuct t                                            21

<210> SEQ ID NO 115
<211> LENGTH: 21
<212> TYPE: DNA
<213> ORGANISM: Homo sapiens

<400> SEQUENCE: 115
aatatcctcg tgaagaacga c                                            21

<210> SEQ ID NO 116
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 116
uauccucgug aagaacgact t                                            21

<210> SEQ ID NO 117
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 117
gucguucuuc acgaggauat t                                            21

<210> SEQ ID NO 118
```

```
<211> LENGTH: 21
<212> TYPE: DNA
<213> ORGANISM: Homo sapiens

<400> SEQUENCE: 118
aactgcaaga tacatggctc c                                              21

<210> SEQ ID NO 119
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 119
cugcaagaua cauggcuccu t                                              21

<210> SEQ ID NO 120
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 120
ggagccaugu aucuugcagt t                                              21

<210> SEQ ID NO 121
<211> LENGTH: 21
<212> TYPE: DNA
<213> ORGANISM: Homo sapiens

<400> SEQUENCE: 121
aagatacatg gctccagaag t                                              21

<210> SEQ ID NO 122
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 122
gauacauggc uccagaagut t                                              21

<210> SEQ ID NO 123
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 123
acuucuggag ccauguauct t                                              21

<210> SEQ ID NO 124
<211> LENGTH: 21
<212> TYPE: DNA
<213> ORGANISM: Homo sapiens

<400> SEQUENCE: 124
aagtcctaga ttccaggatg a                                              21

<210> SEQ ID NO 125
<211> LENGTH: 21
<212> TYPE: DNA
```

<213> ORGANISM: Artificial Sequence
<220> FEATURE:
<223> OTHER INFORMATION: Synthetic oligonucleotide

<400> SEQUENCE: 125
guccuagaau ccaggaugat t                                           21

<210> SEQ ID NO 126
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 126
ucauccugga uucuaggact t                                           21

<210> SEQ ID NO 127
<211> LENGTH: 21
<212> TYPE: DNA
<213> ORGANISM: Homo sapiens

<400> SEQUENCE: 127
aatccaggat gaatttggag a                                           21

<210> SEQ ID NO 128
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 128
uccaggauga auuuggagat t                                           21

<210> SEQ ID NO 129
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 129
ucuccaaauu cauccuggat t                                           21

<210> SEQ ID NO 130
<211> LENGTH: 21
<212> TYPE: DNA
<213> ORGANISM: Homo sapiens

<400> SEQUENCE: 130
aatttggaga atgctgagtc c                                           21

<210> SEQ ID NO 131
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 131
uuuggagaau gcugagucct t                                           21

<210> SEQ ID NO 132
<211> LENGTH: 21
<212> TYPE: DNA

```
<213> ORGANISM: Artificial Sequence
<220> FEATURE:
<223> OTHER INFORMATION: Synthetic oligonucleotide

<400> SEQUENCE: 132
ggacucagca uucuccaaat t                                              21

<210> SEQ ID NO 133
<211> LENGTH: 21
<212> TYPE: DNA
<213> ORGANISM: Homo sapiens

<400> SEQUENCE: 133
aatgctgagt ccttcaagca g                                              21

<210> SEQ ID NO 134
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 134
ugcugagucc uucaagcagt t                                              21

<210> SEQ ID NO 135
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 135
cugcuugaag gacucagcat t                                              21

<210> SEQ ID NO 136
<211> LENGTH: 21
<212> TYPE: DNA
<213> ORGANISM: Homo sapiens

<400> SEQUENCE: 136
aaatgacatc tcgctgtaat g                                              21

<210> SEQ ID NO 137
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 137
augacaucuc gcuguaaugt t                                              21

<210> SEQ ID NO 138
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 138
cauuacagcg agaugucaut t                                              21

<210> SEQ ID NO 139
<211> LENGTH: 21
<212> TYPE: DNA
```

```
<213> ORGANISM: Homo sapiens

<400> SEQUENCE: 139
aatgcagtgg gagaagtaaa a                                              21

<210> SEQ ID NO 140
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 140
ugcaguggga gaaguaaaat t                                              21

<210> SEQ ID NO 141
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 141
uuuuacuucu cccacugcat t                                              21

<210> SEQ ID NO 142
<211> LENGTH: 21
<212> TYPE: DNA
<213> ORGANISM: Homo sapiens

<400> SEQUENCE: 142
aagattatga gcctccattt g                                              21

<210> SEQ ID NO 143
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 143
gauuaugagc cuccauuugt t                                              21

<210> SEQ ID NO 144
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 144
caaauggagg cucauaauct t                                              21

<210> SEQ ID NO 145
<211> LENGTH: 21
<212> TYPE: DNA
<213> ORGANISM: Homo sapiens

<400> SEQUENCE: 145
aaagcatgaa ggacaacgtg t                                              21

<210> SEQ ID NO 146
<211> LENGTH: 21
<212> TYPE: DNA
<213> ORGANISM: Artificial Sequence
<220> FEATURE:
```

```
<223> OTHER INFORMATION: Synthetic oligonucleotide

<400> SEQUENCE: 146
agcaugaagg acaacgugut t                                              21

<210> SEQ ID NO 147
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 147
acacguuguc cuucaugcut t                                              21

<210> SEQ ID NO 148
<211> LENGTH: 21
<212> TYPE: DNA
<213> ORGANISM: Homo sapiens

<400> SEQUENCE: 148
aaggacaacg tgttgagaga t                                              21

<210> SEQ ID NO 149
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 149
ggacaacgug uugagagaut t                                              21

<210> SEQ ID NO 150
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 150
aucucucaac acguugucct t                                              21

<210> SEQ ID NO 151
<211> LENGTH: 21
<212> TYPE: DNA
<213> ORGANISM: Homo sapiens

<400> SEQUENCE: 151
aaattcccag cttctggctc a                                              21

<210> SEQ ID NO 152
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 152
auucccagcu ucuggcucat t                                              21

<210> SEQ ID NO 153
<211> LENGTH: 21
<212> TYPE: DNA
<213> ORGANISM: Artificial Sequence
<220> FEATURE:
```

```
<223> OTHER INFORMATION: Synthetic oligonucleotide

<400> SEQUENCE: 153
ugagccagaa gcugggaaut t                                              21

<210> SEQ ID NO 154
<211> LENGTH: 21
<212> TYPE: DNA
<213> ORGANISM: Homo sapiens

<400> SEQUENCE: 154
aagacggctc cctaaacact a                                              21

<210> SEQ ID NO 155
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 155
gacggcuccc uaaacacuat t                                              21

<210> SEQ ID NO 156
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 156
uaguguuuag ggagccguct t                                              21

<210> SEQ ID NO 157
<211> LENGTH: 21
<212> TYPE: DNA
<213> ORGANISM: Homo sapiens

<400> SEQUENCE: 157
aagaatataa caccagcaat c                                              21

<210> SEQ ID NO 158
<211> LENGTH: 21
<212> TYPE: DNA
<213> ORGANISM: Homo sapiens

<400> SEQUENCE: 158
aagcatgaga acatactcca g                                              21

<210> SEQ ID NO 159
<211> LENGTH: 2090
<212> TYPE: DNA
<213> ORGANISM: Homo sapiens
<220> FEATURE:
<221> NAME/KEY: CDS
<222> LOCATION: (336)..(2039)

<400> SEQUENCE: 159
gttggcgagg agtttcctgt ttcccccgca gcgctgagtt gaagttgagt gagtcactcg      60
cgcgcacgga gcgacgacac ccccgcgcgt gcacccgctc gggacaggag ccggactcct     120
gtgcagcttc cctcggccgc cggggggcct cccgcgcctc gccggcctcc aggcccctcc     180
tggctgcgca gcgggcgcca catctggccc gcacatctgc gctgccggcc cggcgcgggg     240
tccggagagg gcgcggcgcg gagcgcagcc agggggtccgg gaaggcgccg tccgtgcgct     300
```

```
gggggctcgg tctatgacga gcagcggggt ctgcc atg ggt cgg ggg ctg ctc        353
                                       Met Gly Arg Gly Leu Leu
                                       1               5 agg ggc ctg tgg ccg ctg cac atc gtc ctg tgg acg cgt atc gcc agc       401
Arg Gly Leu Trp Pro Leu His Ile Val Leu Trp Thr Arg Ile Ala Ser
        10                  15                  20 acg atc cca ccg cac gtt cag aag tcg gtt aat aac gac atg ata gtc       449
Thr Ile Pro Pro His Val Gln Lys Ser Val Asn Asn Asp Met Ile Val
                25                  30                  35 act gac aac aac ggt gca gtc aag ttt cca caa ctg tgt aaa ttt tgt       497
Thr Asp Asn Asn Gly Ala Val Lys Phe Pro Gln Leu Cys Lys Phe Cys
 40                  45                  50 gat gtg aga ttt tcc acc tgt gac aac cag aaa tcc tgc atg agc aac       545
Asp Val Arg Phe Ser Thr Cys Asp Asn Gln Lys Ser Cys Met Ser Asn
55                  60                  65                  70 tgc agc atc acc tcc atc tgt gag aag cca cag gaa gtc tgt gtg gct       593
Cys Ser Ile Thr Ser Ile Cys Glu Lys Pro Gln Glu Val Cys Val Ala
                75                  80                  85 gta tgg aga aag aat gac gag aac ata aca cta gag aca gtt tgc cat       641
Val Trp Arg Lys Asn Asp Glu Asn Ile Thr Leu Glu Thr Val Cys His
                90                  95                 100 gac ccc aag ctc ccc tac cat gac ttt att ctg gaa gat gct gct tct       689
Asp Pro Lys Leu Pro Tyr His Asp Phe Ile Leu Glu Asp Ala Ala Ser
                105                 110                 115 cca aag tgc att atg aag gaa aaa aaa aag cct ggt gag act ttc ttc       737
Pro Lys Cys Ile Met Lys Glu Lys Lys Lys Pro Gly Glu Thr Phe Phe
    120                 125                 130 atg tgt tcc tgt agc tct gat gag tgc aat gac aac atc atc ttc tca       785
Met Cys Ser Cys Ser Ser Asp Glu Cys Asn Asp Asn Ile Ile Phe Ser
135                 140                 145                 150 gaa gaa tat aac acc agc aat cct gac ttg ttg cta gtc ata ttt caa       833
Glu Glu Tyr Asn Thr Ser Asn Pro Asp Leu Leu Leu Val Ile Phe Gln
                155                 160                 165 gtg aca ggc atc agc ctc ctg cca cca ctg gga gtt gcc ata tct gtc       881
Val Thr Gly Ile Ser Leu Leu Pro Pro Leu Gly Val Ala Ile Ser Val
                170                 175                 180 atc atc atc ttc tac tgc tac cgc gtt aac cgg cag cag aag ctg agt       929
Ile Ile Ile Phe Tyr Cys Tyr Arg Val Asn Arg Gln Gln Lys Leu Ser
            185                 190                 195 tca acc tgg gaa acc ggc aag acg cgg aag ctc atg gag ttc agc gag       977
Ser Thr Trp Glu Thr Gly Lys Thr Arg Lys Leu Met Glu Phe Ser Glu
    200                 205                 210 cac tgt gcc atc atc ctg gaa gat gac cgc tct gac atc agc tcc acg      1025
His Cys Ala Ile Ile Leu Glu Asp Asp Arg Ser Asp Ile Ser Ser Thr
215                 220                 225                 230 tgt gcc aac aac atc aac cac aac aca gag ctg ctg ccc att gag ctg      1073
Cys Ala Asn Asn Ile Asn His Asn Thr Glu Leu Leu Pro Ile Glu Leu
                235                 240                 245 gac acc ctg gtg ggg aaa ggt cgc ttt gct gag gtc tat aag gcc aag      1121
Asp Thr Leu Val Gly Lys Gly Arg Phe Ala Glu Val Tyr Lys Ala Lys
                250                 255                 260 ctg aag cag aac act tca gag cag ttt gag aca gtg gca gtc aag atc      1169
Leu Lys Gln Asn Thr Ser Glu Gln Phe Glu Thr Val Ala Val Lys Ile
                265                 270                 275 ttt ccc tat gag gag tat gcc tct tgg aag aca gag aag gac atc ttc      1217
Phe Pro Tyr Glu Glu Tyr Ala Ser Trp Lys Thr Glu Lys Asp Ile Phe
            280                 285                 290 tca gac atc aat ctg aag cat gag aac ata ctc cag ttc ctg acg gct      1265
Ser Asp Ile Asn Leu Lys His Glu Asn Ile Leu Gln Phe Leu Thr Ala
295                 300                 305                 310
```

```
gag gag cgg aag acg gag ttg ggg aaa caa tac tgg ctg atc acc gcc    1313
Glu Glu Arg Lys Thr Glu Leu Gly Lys Gln Tyr Trp Leu Ile Thr Ala
            315                 320                 325 ttc cac gcc aag ggc aac cta cag gag tac ctg acg cgg cat gtc atc    1361
Phe His Ala Lys Gly Asn Leu Gln Glu Tyr Leu Thr Arg His Val Ile
        330                 335                 340 agc tgg gag gac ctg cgc aag ctg ggc agc tcc ctc gcc cgg ggg att    1409
Ser Trp Glu Asp Leu Arg Lys Leu Gly Ser Ser Leu Ala Arg Gly Ile
    345                 350                 355 gct cac ctc cac agt gat cac act cca tgt ggg agg ccc aag atg ccc    1457
Ala His Leu His Ser Asp His Thr Pro Cys Gly Arg Pro Lys Met Pro
360                 365                 370 atc gtg cac agg gac ctc aag agc tcc aat atc ctc gtg aag aac gac    1505
Ile Val His Arg Asp Leu Lys Ser Ser Asn Ile Leu Val Lys Asn Asp
375                 380                 385                 390 cta acc tgc tgc ctg tgt gac ttt ggg ctt tcc ctg cgt ctg gac cct    1553
Leu Thr Cys Cys Leu Cys Asp Phe Gly Leu Ser Leu Arg Leu Asp Pro
            395                 400                 405 act ctg tct gtg gat gac ctg gct aac agt ggg cag gtg gga act gca    1601
Thr Leu Ser Val Asp Asp Leu Ala Asn Ser Gly Gln Val Gly Thr Ala
        410                 415                 420 aga tac atg gct cca gaa gtc cta gaa tcc agg atg aat ttg gag aat    1649
Arg Tyr Met Ala Pro Glu Val Leu Glu Ser Arg Met Asn Leu Glu Asn
    425                 430                 435 gct gag tcc ttc aag cag acc gat gtc tac tcc atg gct ctg gtg ctc    1697
Ala Glu Ser Phe Lys Gln Thr Asp Val Tyr Ser Met Ala Leu Val Leu
440                 445                 450 tgg gaa atg aca tct cgc tgt aat gca gtg gga gaa gta aaa gat tat    1745
Trp Glu Met Thr Ser Arg Cys Asn Ala Val Gly Glu Val Lys Asp Tyr
455                 460                 465                 470 gag cct cca ttt ggt tcc aag gtg cgg gag cac ccc tgt gtc gaa agc    1793
Glu Pro Pro Phe Gly Ser Lys Val Arg Glu His Pro Cys Val Glu Ser
            475                 480                 485 atg aag gac aac gtg ttg aga gat cga ggg cga cca gaa att ccc agc    1841
Met Lys Asp Asn Val Leu Arg Asp Arg Gly Arg Pro Glu Ile Pro Ser
        490                 495                 500 ttc tgg ctc aac cac cag ggc atc cag atg gtg tgt gag acg ttg act    1889
Phe Trp Leu Asn His Gln Gly Ile Gln Met Val Cys Glu Thr Leu Thr
    505                 510                 515 gag tgc tgg gac cac gac cca gag gcc cgt ctc aca gcc cag tgt gtg    1937
Glu Cys Trp Asp His Asp Pro Glu Ala Arg Leu Thr Ala Gln Cys Val
520                 525                 530 gca gaa cgc ttc agt gag ctg gag cat ctg gac agg ctc tcg ggg agg    1985
Ala Glu Arg Phe Ser Glu Leu Glu His Leu Asp Arg Leu Ser Gly Arg
535                 540                 545                 550 agc tgc tcg gag gag aag att cct gaa gac ggc tcc cta aac act acc    2033
Ser Cys Ser Glu Glu Lys Ile Pro Glu Asp Gly Ser Leu Asn Thr Thr
            555                 560                 565 aaa tag ctcttatggg gcaggctggg catgtccaaa gaggctgccc ctctcaccaa a   2090
Lys

<210> SEQ ID NO 160
<211> LENGTH: 567
<212> TYPE: PRT
<213> ORGANISM: Homo sapiens

<400> SEQUENCE: 160

Met Gly Arg Gly Leu Leu Arg Gly Leu Trp Pro Leu His Ile Val Leu
1               5                   10                  15

Trp Thr Arg Ile Ala Ser Thr Ile Pro Pro His Val Gln Lys Ser Val
```

```
                20                  25                  30
Asn Asn Asp Met Ile Val Thr Asp Asn Gly Ala Val Lys Phe Pro
            35                  40                  45
Gln Leu Cys Lys Phe Cys Asp Val Arg Phe Ser Thr Cys Asp Asn Gln
        50                  55                  60
Lys Ser Cys Met Ser Asn Cys Ser Ile Thr Ser Ile Cys Glu Lys Pro
65                  70                  75                  80
Gln Glu Val Cys Val Ala Val Trp Arg Lys Asn Asp Glu Asn Ile Thr
                85                  90                  95
Leu Glu Thr Val Cys His Asp Pro Lys Leu Pro Tyr His Asp Phe Ile
                100                 105                 110
Leu Glu Asp Ala Ala Ser Pro Lys Cys Ile Met Lys Glu Lys Lys
            115                 120                 125
Pro Gly Glu Thr Phe Phe Met Cys Ser Cys Ser Ser Asp Glu Cys Asn
        130                 135                 140
Asp Asn Ile Ile Phe Ser Glu Glu Tyr Asn Thr Ser Asn Pro Asp Leu
145                 150                 155                 160
Leu Leu Val Ile Phe Gln Val Thr Gly Ile Ser Leu Leu Pro Pro Leu
                165                 170                 175
Gly Val Ala Ile Ser Val Ile Ile Phe Tyr Cys Tyr Arg Val Asn
            180                 185                 190
Arg Gln Gln Lys Leu Ser Ser Thr Trp Glu Thr Gly Lys Thr Arg Lys
        195                 200                 205
Leu Met Glu Phe Ser Glu His Cys Ala Ile Ile Leu Glu Asp Asp Arg
        210                 215                 220
Ser Asp Ile Ser Ser Thr Cys Ala Asn Asn Ile Asn His Asn Thr Glu
225                 230                 235                 240
Leu Leu Pro Ile Glu Leu Asp Thr Leu Val Gly Lys Gly Arg Phe Ala
                245                 250                 255
Glu Val Tyr Lys Ala Lys Leu Lys Gln Asn Thr Ser Glu Gln Phe Glu
            260                 265                 270
Thr Val Ala Val Lys Ile Phe Pro Tyr Glu Glu Tyr Ala Ser Trp Lys
        275                 280                 285
Thr Glu Lys Asp Ile Phe Ser Asp Ile Asn Leu Lys His Glu Asn Ile
        290                 295                 300
Leu Gln Phe Leu Thr Ala Glu Glu Arg Lys Thr Glu Leu Gly Lys Gln
305                 310                 315                 320
Tyr Trp Leu Ile Thr Ala Phe His Ala Lys Gly Asn Leu Gln Glu Tyr
                325                 330                 335
Leu Thr Arg His Val Ile Ser Trp Glu Asp Leu Arg Lys Leu Gly Ser
            340                 345                 350
Ser Leu Ala Arg Gly Ile Ala His Leu His Ser Asp His Thr Pro Cys
        355                 360                 365
Gly Arg Pro Lys Met Pro Ile Val His Arg Asp Leu Lys Ser Ser Asn
        370                 375                 380
Ile Leu Val Lys Asn Asp Leu Thr Cys Cys Leu Cys Asp Phe Gly Leu
385                 390                 395                 400
Ser Leu Arg Leu Asp Pro Thr Leu Ser Val Asp Asp Leu Ala Asn Ser
                405                 410                 415
Gly Gln Val Gly Thr Ala Arg Tyr Met Ala Pro Glu Val Leu Glu Ser
            420                 425                 430
Arg Met Asn Leu Glu Asn Ala Glu Ser Phe Lys Gln Thr Asp Val Tyr
        435                 440                 445
```

```
Ser Met Ala Leu Val Leu Trp Glu Met Thr Ser Arg Cys Asn Ala Val
    450                 455                 460

Gly Glu Val Lys Asp Tyr Glu Pro Pro Phe Gly Ser Lys Val Arg Glu
465                 470                 475                 480

His Pro Cys Val Glu Ser Met Lys Asp Asn Val Leu Arg Asp Arg Gly
                485                 490                 495

Arg Pro Glu Ile Pro Ser Phe Trp Leu Asn His Gln Gly Ile Gln Met
                500                 505                 510

Val Cys Glu Thr Leu Thr Glu Cys Trp Asp His Asp Pro Glu Ala Arg
        515                 520                 525

Leu Thr Ala Gln Cys Val Ala Glu Arg Phe Ser Glu Leu Glu His Leu
    530                 535                 540

Asp Arg Leu Ser Gly Arg Ser Cys Ser Glu Glu Lys Ile Pro Glu Asp
545                 550                 555                 560

Gly Ser Leu Asn Thr Thr Lys
                565

<210> SEQ ID NO 161
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 161
gcugaagcag aacacuucat t                                           21
```

SILENCING OF TGFβ TYPE II RECEPTOR EXPRESSION BY SIRNA

INTRODUCTION

This application is a continuation of U.S. Ser. No. 10/567,958 filed May 10, 2006 now abandoned, which is the U.S. National Phase of PCT/US2004/025984 filed Aug. 10, 2004; which claims priority to U.S. Provisional Application Nos. 60/495,161 filed Aug. 13, 2003, 60/517,809 filed Nov. 6, 2003 and 60/561,542 filed Apr. 9, 2004, each of which are herein incorporated by reference in their entireties.

This invention was made with government support under Grant No. EY013605 awarded by NIH. The government has certain rights in the invention.

FIELD OF THE INVENTION

The present invention is directed to methods and compositions for silencing transforming growth factor beta type II receptor (TGFβRII) expression. More particularly the present invention describes methods and compositions for reducing such expression using small interfering RNA (siRNA) molecules.

BACKGROUND OF THE INVENTION

Transforming growth factor-β (TGF□) comprises a family of structurally related multifunctional cytokines. They have a wide variety of biological actions, including cell growth, differentiation, apoptosis, fibrogenesis and angiogenesis. (Massague et al., *Cancer Surv.* 12, 81-103, (1992), Piek et al., *FASEB J.* 13, 2105-2124, (1999), Border & Noble *N. Engl. J. Med.* 331, 1286-1292 (1994); Govinda and Bhoola, *Pharmacol. Ther.* 98:257-265 (2003); Cusiefen et al., *Cornea* 19:526-533; Sakimoto et al., *Gene Therapy* 7:1915-1924 (2000)) TGFβ is typically secreted in a biologically latent form. It is activated through a complex process of proteolytic activation and dissociation of latency protein subunits. (Massague, *Annu. Rev. Biochem.* 67, 753-791 (1998)).

The mechanism of action of TGFβ is mediated by its binding to receptors known as TGFβ receptors, types I, II and III. Receptors I and II are transmembrane glycoproteins of 55 and 70 kDa shown to be important in signal transduction. The TGFβ ligand binding site for these receptors is extracellular. The mechanism by which the signaling is thought to be achieved is via activation of phosphorylation of transcription factors known as Smads. (Massague & Wotton, EMBO J. 19, 1745-1754 (1999)).

TGFβ has emerged as a key component of the fibrogenic response to wounding and is upregulated during many different types of wound healing in tissues such as the eye, liver, and skin. (Border & Noble, *N. Engl. J. Med.* 331, 1286-1292 (1994), Connor et al., *J. Clin. Invest.* 83, 1661-1666 (1989), McCormick et al., *J. Immunol.* 163, 5693-5699 (1999), Shah et al., *J. Cell Sci.* 108, 985-1002 (1995)). In the eye, of the three human isoforms (TGFβ1, TGFβ2, and TGFβ3), TGFβ2 is the predominant one. (Lutty et al., *Invest. Opthalmol. Vis. Sci.* 34, 477-487 (1993), Pasquale et al., *Invest. Opthalmol. Vis. Sci.* 34, 23-30 (1993)). TGFβs have been implicated in several scarring processes including proliferative vitreoretinopathy, (Kon et al., *Invest. Opthalmol. Vis. Sci.* 40, 705-712 (1999)), cataract formation, (Hales et al., *Invest. Opthalmol. Vis. Sci.* 36, 1709-1713 (1989)), corneal opacities, (Chen et al., *Invest. Opthalmol. Vis. Sci.* 41, 4108-4116 (2000)), and conjunctival wound healing, (Cordeiro, *Clin. Sci.* 104, 181-187 (2003)) especially that occurring after filtration surgery for a major blinding disease, glaucoma. In addition, TGFβ in conjunction with connective tissue growth factor (CTGF) has an important role in angiogenesis (Abreu et al., *Nature Cell Biol.* 4:599-604 (2002)). Furthermore, recent studies have shown that TGF may actually be involved in the pathogenesis of primary open angle glaucoma (Inatani et al., *Graefes Arch. Clin. Exp. Opthalmol.* 239(2):109-13, 2001; Ochiai et al., *Jap. J. Opthalmol.* 46(3):249-53, 2002; Gattanka et al., *Invest. Opthalmol. Vis. Sci.* 45(1):153-8, 2004).

In glaucoma filtration surgery, excessive postoperative scarring at the wound site significantly reduces surgical success. (Migdal et al, *Ophthalmology* 101, 1651-1656 (1994), Addicks et al., *Opthalmol.* 101, 795-798 (1983)). Although anti-scarring agents such as mitomycin-C and 5-fluorouracil could help prevent postsurgical scarring and improve glaucoma surgical outcome, (Khaw et al., *Arch. Opthalmol.* 111, 263-267 (1993), Cordeiro et al., *Invest. Opthalmol. Vis. Sci.* 40, 1975-1982 (1999)) they do so by causing widespread fibroblast cell death and are associated with severe and potentially blinding complications. (Crowston et al. 449-454 (1998), Stamper et al., *Am. J. Opthalmol.* 114, 544-553 (1992)). In light of the role of TGFβ in the wound repair process, alternative strategies (Codeiro, *Prog. Retin. Eye Res.* 21, 75-89 (2002)) such as antibodies (Cordeior et al., *Invest. Opthalmol. Vis. Sci.* 40, 2225-2234 (1999), Mead et al., *Invest. Opthalmol. Vis. Sci.* 44, 3394-3401 (2003)) to TGFβ and antisense oligonucleotides (Cordeior, et al., *Gene Therapy* 10, 59-70 (2003)) have been used to block TGFβ action. However these techniques remain inadequate for the treatment of the debilitating scarification that occurs in many glaucoma. For example, use of antisense therapy is poorly effective in treating various disorders because antisense molecules are known to induce an interferon response in the patient. Use of antibody-based therapies are marred by the need to generate specific antibodies against particular epitopes of a given antigen. Thus, there remains a need to identify new methods of intervening in disorders that result from an over-expression or even mere presence of TGFβ type II receptor.

SUMMARY OF THE INVENTION

The present invention is directed to the use of siRNA both in vitro and in vivo to regulate the TGFβ type II receptor (TGFβ RII) level and modulate wound responses and angiogenesis in a mammal. The RNA interference-based methods of the present invention have a wide-ranging application, extending from the eye to other organs and tissues throughout the body.

In certain embodiments, the invention is directed to methods and compositions for promoting wound healing, reducing fibrosis and/or reducing angiogenesis in a mammal by administering to the mammal a composition comprising siRNA molecules that target the type II receptor of TGFβ.

The siRNA molecules of the present invention may be delivered, in a therapeutically effective amount, locally at the site of the wound or alternatively may be administered systemically. In certain embodiments, therapeutically effective siRNA compositions may be administered alone or alternatively, the siRNA molecule-based therapeutic compositions may be administered as part of a therapeutic regimen that comprises other wound-healing compositions.

In particularly preferred embodiments, the disorder to be treated by the siRNA based therapeutic compositions of the present invention is glaucoma. However, it should be understood that the siRNA compositions of the present invention may be used in the treatment of any disorder in which signaling through the TGFβ type II receptor is implicated. In addition to glaucoma filtration surgery, the compositions of the present invention may be used to promote healing, with a reduction in scarring, of any other ophthalmic surgery, which may include but is not limited to, cataract extraction, with or without lens replacement; corneal transplants, to treat viral infection or penetrating keratoplasty (PKP); and radial keratotomy and other types of surgery to correct refraction. The compositions and methods of the invention also may be used to treat ocular disorders such as, e.g., retinal wounds such as retinal detachments and tears, retinal vacuolar disorder, retinal neovascularization, diabetic retinopathy, corneal wounds such as corneal epithelial wounds, corneal neovascularization, corneal ulcers, macular holes, macular degeneration, secondary cataracts, corneal disease, dry eye/Sjogren's syndrome and uveitis. These disorders include wound healing disorders, proliferative disorders, anti-degenerative disorders and anti-angiogenesis disorders that effect the eye.

In each of the above methods, the method involves administering to the mammal an amount of the siRNA composition in an amount effective to stabilize or improve vision. Retinal disorders, which are characterized by increased connective or fibrous tissue, also may be treated using methods which comprise the steps of removing the vitreous humor from the eye; removing the epiretinal membrane, if present, from the eye; and administering a composition comprising the siRNA compositions of the invention by cannula to place the therapeutic composition immediately over the portion of the retina requiring treatment.

In certain other embodiments, the siRNA composition may be administered by intraocular injection or by application to the cornea. Such corneal application may be achieved using eye drops or a timed release capsule placed in the cul de sac.

In another embodiment, there is provided a method for treating a mammal for ocular neovascularization, said method comprising administering to a mammal an effective amount of the siRNA compositions of the present invention.

Other non-ocular disorders that may be treated using the siRNA-based methods of the present invention include but are not limited to fibroproliferative disorders such as those selected from the group consisting of diabetic nephropathy, glomerulonephritis, proliferative vitreoretinopathy, liver cirrhosis, biliary fibrosis, and myelofibrosis, post-radiation fibrosis. Connective tissue disorders such as rheumatoid arthritis, scleroderma, myelofibrosis, and hepatic, and pulmonary fibrosis also may be treated. Disorders involving defective T-cell response, such as trypanosomal infection or viral infections such as human immunosuppression virus, human T cell lymphotrophic virus, lymphocytic choroiomeningitis virus and hepatitis may be treated. siRNA methods may be used to treat patients with cancer, including patients with prostate cancer, ovarian cancer, plasmacytoma and glioblastoma. siRNA may be used to treat patient with collagen vascular diseases such as progressive systemic sclerosis (PSS), polymyositis, dermatomyositis and systemic lupus erythamatosus.

In addition, siRNA-based methods may be used to treat wounds other than those induce by ocular trauma, disorders or surgery. Surgical incisions in general, trauma-induced lacerations, fibrosis due to radiation therapy and wounds involving the peritoneum may be treated. Scarring resulting from restenosis of blood vessels, hypertrophic scars and keloids may also be treated with siRNA methods.

Particularly preferred siRNA molecules include 21-23 bases. Four specific sequences for the TGFβRII siRNA were derived from the human TGFβRII sequence (Genbank Accession Number: M85079) and were designated as NK1, NK2, SS1 and SS2. The target sequences (5' to 3') are set out as below, with the position of the first nucleotide in the human TGFβII receptor sequence (from M85079) shown in parenthesis. The corresponding commercially synthesized siRNA duplexes are also set out below:

| Target Sequence 5' to 3' Nucleotide number in parenthesis | siRNA duplex |
|---|---|
| NK1 (529) AATCCTGCATGAGCAACTGCA (SEQ ID NO: 1) | UCCUGCAUGAGCAACUGCAdTdT dTdTAGGACGUACUCGUUGACGU (SEQ ID NOS: 5-6) |
| NK2 (1113) AAGGCCAAGCTGAAGCAGAAC (SEQ ID NO: 2) | GGCCAAGCUGAAGCAGAACdTdT dTdTCCGGUUCGACUUCGUCUUG (SEQ ID NOS: 7-8) |
| SS1 (1253) AGCATGAGAACATACTCCAG (SEQ ID NO: 3) | GCAUGAGAACAUACUCCAGdTdT dTdTCGUACUCUUGUAUGAGGUC (SEQ ID NO: 9-10) |
| SS2 (948) AAGACGCGGAAGCTCATGGAG (SEQ ID NO: 4) | GACGCGGAAGCUCAUGGAGdTdT dTdTCUGCGCCUUCGAGUACCUC (SEQ ID NO: 11-12) |

It should be understood that those of skill in the art will be able to produce additional siRNA molecules surrounding positions 529, 1113, 1253 and 948 of the human TGFβRII gene sequence at Genbank Accession Number: M85079. It should be understood that the siRNA molecules of the invention may be conveniently formulated into pharmaceutical formulations using methods known to those of skill in the art. Such pharmaceutical compositions also may comprise other non-siRNA based therapeutic agents for the therapeutic intervention of the particular disorder being treated. Other wound healing compositions include anti-cancer drugs Mitomycin and 5-fluorouracil, *agaricus bisporus* lectin, metallocomplexes such as zinc-desferrioxaminde or gallium-desferrioxamine, methyl xanthine derivatives such as pentoxifylline, collagen-based sealants such as GE Amidon Oxyde, agents that inhibit fibroblast growth factors and connective tissue growth factor, and matrix metalloproteinase inhibitors such as ilomastat. Other anti-angiogenic agents include inhibitors of vascular endothelial growth factor (VEGF) and antiangiogenic steroids. Inhibitors of VEGF include siRNA molecules targeting VEGF or its receptor.

Other features and advantages of the present invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE DRAWINGS

The following drawings form part of the present specification and are included to further illustrate aspects of the present invention. The invention may be better understood by reference to the drawings in combination with the detailed description of the specific embodiments presented herein.

FIG. 3A-3G provides target sequences in the TGFβ type II receptor sequence and the corresponding siRNA molecule sequences. The nucleotide numbers refer to the location in the type II TGF-β receptor sequence (Genbank Accession Number: M85079). The GC content refers to the content of guanine and cytosines (GC) within the target sequence.

FIG. 4. Inhibition of TGFβRII using siRNA on HUVEC cells. Human umbical vein endothelial cells (HUVEC) were plated at 3×10-5 and allowed to grow into confluent monolayers. Following day the cells were treated with (a) control (TKO reagent only), (b) scrambled (c) NK1 siRNA oligonucleotides, (d) SS1 siRNA oligonucleotides, all in the TKO reagent. Images were taken 48 hours post RNAi treatment. e, f, g, and h are corresponding DAPI nuclear staining of the cells in panels a, b, c, and d respectively. Scale bar is 10 microns.

DETAILED DESCRIPTION OF THE PREFERRED EMBODIMENTS OF THE INVENTION

Figure 1:
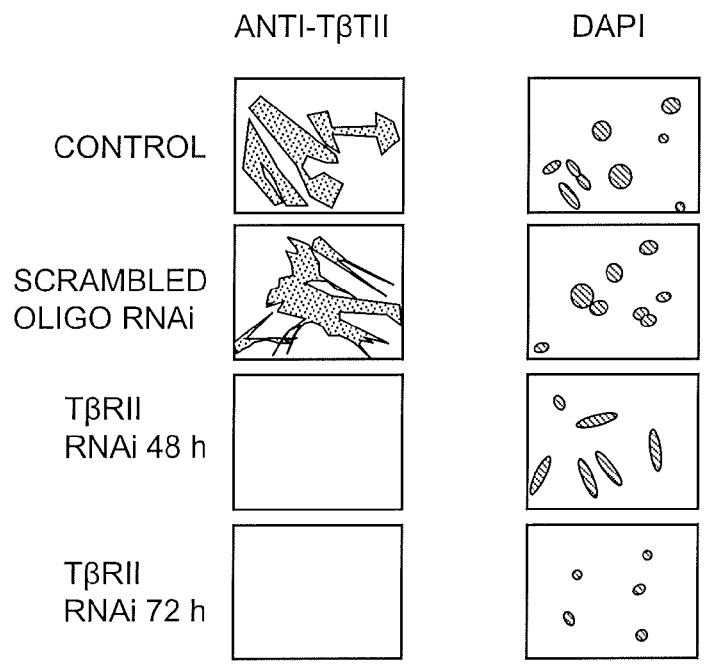
FIG. 1. Inhibition of TGFβ type II receptor expression by siRNA. Immunofluorescence analysis of human corneal fibroblasts untreated (1st row), or treated with scrambled siRNA (2nd row) or 100 nM NK1 (3rd and 4th rows) was performed to visualize TGFβRII receptor expression (left column). Staining of nuclei using DAPI stain is shown in the right column. Note the large reduction in staining of cells treated with NK1 siRNA at 48 (3rd row, left column) and 72 h (4th row, left column) compared to control cells (1st and 2nd rows, left column).

There is a need to develop new therapies for reducing scarring that result during wound healing. TGFβ is known to be involved in the fibrogenic response in wound healing, and inhibition of TGFβ-induced activities may be therapeutically effective for reducing fibrosis and scarring. The present invention provides specific siRNA compositions for use in methods of promoting wound healing and for reducing scarring as a result of wound healing. In addition, the present invention provides specific siRNA compounds for use in methods of inhibiting angiogenesis. These compositions are described in further detail herein.

Definitions

The term RNA interference (RNAi) refers to post-transcriptional gene silencing induced by the introduction of double stranded RNA.

The term small interfering RNAs (siRNAs) refers to nucleotides of 19-23 bases in length which incorporate into an RNA-induced silencing complex in order to guide the complex to homologous endogenous mRNA for cleavage and degradation of TGFβRII and that mRNA.

The term transforming growth factor (TGFβ) refers to a family of peptide growth factors including five member, numbered 1 through 5.

The term TGFβ receptors refers to cell surface proteins, of which three (Type I, Type II and Type III) are known in mammals. The TGFβ type II receptor (TGFβRII) is a membrane bound protein with an intracellular domain, a transmembrane domain and extracellular domain that binds to TGFβ. As reviewed in Massague et al., *Annu. Rev. Biochem.* 67: 753-791, (1998) incorporated herein by reference.

The term therapeutically effective amount refers the amount of a siRNA molecule which effectively suppresses expression of the TGFβRII protein in a mammal in need.

Role of TGFβ Family in Wound Healing

Transforming growth factor-β (TGFβ) family of cytokines is an important mediator in the wound healing process in various tissues. In the eye, TGFβ has been implicated in the corneal haze and scarring at the wound site following glaucoma surgery. TGFβ has also been associated with diabetic retinopathy, proliferative vitreoretinopathy and macular degeneration. The inventors designed small interfering RNAs (siRNAs) targeting the type II receptor of TGFβ and found that these RNA fragments were effective in abrogating the receptor protein and transcript in cultured human corneal fibroblasts. TGFβ-mediated processes such as fibronectin assembly and cell migration were inhibited. The siRNAs, when introduced subconjunctivally into mouse eyes, were also efficacious in reducing the inflammatory response and matrix deposition. These findings indicate that siRNAs can be successfully delivered both in vitro and in vivo to regulate the TGFβ type II receptor level and modulate wound response. The RNA interference technology may have a wide-ranging application, extending from the eye to other organs and tissues throughout the body.

In addition to wound healing, TGFβ is known to play an important role in the regulation of growth and differentiation of many cell types. As TGFβ is also known to control the accumulation of matrix proteins such as collagen, fibronectin, thrombospondin, osteopontin, proteoglycans and glycosaminoglycans, it is thought to contribute to carcinogenic changes within many organ systems. Therefore, suppression of TGF-βRII gene expression may be a method of treating fibroproliferative disorders, and connective tissue disorders.

TGFβ is also known to induce endothelial tube formation in vitro and is thought to affect the organizational process of capillary tube that formation in vivo. TGFβ levels are known to be elevated in some cancers such as prostate cancer, ovarian cancer, plasmacytoma and gliablastoma. Furthermore, it is associated with angiogenesis in part by its association with CTGF. Thus, suppression of TGFβRII receptor gene expression may be a method of treating these and other types of cancers, as well as abnormal blood vessel growth.

TGFβ is also known to inhibit the growth to both T- and B-lymphocytes, natural killer cells and lymphokine-activated killer cells. Therefore, in addition to cancers, suppression of TGFβRII gene expression may be a method of treating immune disorders such as AIDS, other viral infections and trypanosomal infections.

In addition, siRNA-based methods may be used to treat wounds other than those induce by ocular trauma, disorders or surgery. Surgical incisions in general, trauma-induced lacerations, fibrosis due to radiation therapy and wounds involving the peritoneum may be treated. Scarring resulting from restenosis of blood vessels, hypertrophic scars and keloids may be treated with siRNA methods.

An ocular fibrotic wound healing response represents a significant pathophysiological issue especially as a consequence of the surgical treatment for glaucoma. (Migdal et al. *Ophthalmology* 101, 1651-1656 (1994), Addicks et al., *Arch. Opthalmol.* 101, 795-798 (1983)). Excessive post-operative scarring often leads to failure of the filtration surgery. While the use of antimetabolites such as mitomycin-C and 5-fluorouracil as conjunctival anti-scarring treatments have benefited a number of patients, these agents are associated with potentially blinding complications, such as hypotony maclopathy and infection. (Khaw et al., *Arch. Opthalmol.* 111, 263-267 (1993), Cordeiro et al., *Invest. Opthalmol. Vis. Sci.* 40, 1975-1982 (1999), Crowston et al., *Invest. Opthalmol. Vis. Sci.* 39, 449-454 (1998), Stamper, *Am. J. Opthalmol.* 114, 544-553 (1992)).

Sequestering of mature TGFβ has been a primary target for the development of antifibrotic approaches. Antibodies to TGFβ2 have been demonstrated to significantly reduce conjunctival scarring activity. (Cordeior et al., *Invest. Opthalmol. Vis. Sci.* 40, 2225-2234 (1999), (Mead et al., *Invest. Opthalmol. Vis. Sci.* 44, 3394-3401 (2003)). In addition, modulation of wound healing is observed when antisense oligonucleotides (Cordeior, et al., *Gene Therapy* 10, 59-70 (2003), Shen et al., *Eur. J. Biochem.* 268, 2331-2337 (2001)) or ribozymes (Su et al. *Biochem. Biophys. Res. Commun.* 278, 401-407 (2000), Yamamoto et al., *Circulation* 102, 1308-1314 (2000)) to TGFβ are applied to animal models or cultured cells. Nevertheless, neutralizing antibodies in general exhibit relatively weak effects as these antibodies may not gain full access to the targeted molecule. (Shen et al., *Eur. J. Biochem.* 268, 2331-2337 (2001)). Antisense phosphorothioate oligonucleotides and ribozymes can be effective, but their stability and specificity are at times still in question. The concentration needed is also generally in the μM range. By comparison, the siRNAs are efficacious at 200 nM and are highly specific. Therefore, the present invention specifically contemplates compositions comprising siRNAs at a concentration of 100 nM, 110 nM, 120 nM, 130 nM, 140 nM, 150 nM, 160 nM, 170 nM, 180 nM, 190 nM, 200 nM, 210 nM, 220 nM, 240 nM, 250 nM, 260 nM, 270 nM, 280 nM, 290 nM, and 300 nM or more.

Such compositions of the invention will be used in methods of treating or preventing glaucoma. In addition, recent studies have shown that TGFβ may actually be involved in the pathogenesis of primary open angle glaucoma (Inatani et al., *Graefes Archive for Clinical & Experimental Ophthalmology.* 239(2):109-13, 2001; Ochiai et al., Japanese Journal of Ophthalmology. 46(3):249-53, 2002; Gattanka et al., Invest Opthalmol V is Sci., 45(1):153-8, 2004). Downregulation of the TGFβ receptors in the anterior chamber using siRNA against the TGFβ receptor will be another treatment modality against the actual development or progression of glaucoma. Therefore, the siRNA compositions of the present invention may be used to in treatment methods for glaucoma that has already developed or alternatively may be used prophylactically to prevent glaucoma. Those of skill in the art are aware of animal models for ophthalmologic function and methods and routes of administering therapeutic compositions (e.g., shunts, perfusion, etc.) for the treatment or prevention of glaucoma, see for example, Inatani et al., supra, and Ochiai et al., supra, U.S. Pat. Nos. 6,713,498; 6,699,211; 6,699,210; 6,649,625; 6,595,945; 6,531,128; 6,482,854. Each of these documents are incorporated herein by reference in their entirety.

Furthermore, the use of siRNA against TGFβ receptors will be of value in preventing restenosis of coronary vessels as well as helping to arrest the progression of pulmonary fibrosis and pulmonary scarring from chronic pulmonary obstructive disease as well as renal fibrosis and postoperative scarring in the abdomen and elsewhere in the body. Thus, it is contemplated that the siRNA-based compositions of the invention will be useful as or in conjunction with therapeutic methods for the improvement of circulation and hemostasis in stenotic vessels. Thus, these siRNA compositions may be used alone or in combination with (e.g., during, before or after) by-pass surgery and revascularization procedures (e.g., balloon angioplasty, atherectomy, rotorary ablation (rotoblation)) which serve to improve blood flow by reducing or removing the stenosis. These methods will be useful in reducing the thickness or presence of neointima within the vessel wall which reduces the luminal area of the vessel (i.e., restenosis). For further details of methods and compositions for treating restenosis and stenosis see e.g., U.S. Pat. Nos. 6,663,863; 6,648,881; 6,596,698; 6,520,957; 6,519,488; 6,458,590; 6,491,720; 6,241,718. Each of these documents are incorporated herein by reference in their entirety. These patents are listed to show exemplary teachings in the art for the preparation of stents and medicaments for the treatment of restenosis. The compositions described herein may be used in like manner to the medicaments described therein and also may be used to supplement the treatment methods described in those exemplary patents.

RNA Interference (RNAi) Technology

Variations on RNA interference (RNAi) technology is revolutionizing many approaches to experimental biology, complementing traditional genetic technologies, mimicking the effects of mutations in both cell cultures and in living animals. (McManus & Sharp, *Nat. Rev. Genet.* 3, 737-747 (2002)). The present invention demonstrates that the RNAi technology can be successfully used to regulate wound healing response by targeting the TGFβII receptor gene. The effect is specific and potent. This technology may be applied not only to the conjunctiva, cornea, retina and choroid of the eye, but also in other tissues throughout the body to modulate wound responses in disorders including vascular diseases, hypertension and atherosclerosis. (Yamamoto et al., *Circulation* 102, 1308-1314 (2000)).

In the current study, RNAi was used to target the TGFβ pathway. RNAi, known to occur in animals and eukaryotes, is a process in which double stranded RNA (dsRNA; typically >200 nucleotides in length) triggers the destruction of mRNAs sharing the same sequence. RNAi is initiated by the conversion of dsRNA into 21-23 nucleotide fragments and these small interfering RNAs (siRNAs) direct the degradation of target RNAs. (Elbashir et al., *Nature* 411, 494-498 (2001), Fire et al., *Nature* 391, 199-213 (1998), Hannon, G. J., *Nature* 418, 244-251 (2002)). It has been rapidly adopted to use for silencing genes in a variety of biological systems. (Reich et al., *Mol. Vis.* 9, 210-216 (2003), Song et al., *Nat. Med.* 9, 347-351 (2003)).

RNAi technology may be carried out in mammalian cells by transfection of siRNA molecules. The siRNA molecules may be chemically synthesized, generated by in vitro transcription, or expressed by a vector or PCR product. Commercial providers such as Ambion Inc. (Austin, Tex.), Darmacon Inc. (Lafayette, Colo.), InvivoGen (San Diego, Calif.), and Molecula Research Laboratories, LLC (Herndon, Va.) generate custom siRNA molecules. In addition, commercial kits are available to produce custom siRNA molecules, such as SILENCER™ siRNA Construction Kit (Ambion Inc., Austin, Tex.) or psiRNA System (InvivoGen, San Diego, Calif.). These siRNA molecules may be introduced into cells through transient transfection or by introduction of expression vectors that continually express the siRNA in transient or stably transfected mammalian cells. Transfection may be accomplished by well known methods including methods such as infection, calcium chloride, electroporation, microinjection, lipofection or the DEAE-dextran method or other known techniques. These techniques are well known to those of skill in the art.

The siRNA molecules may be introduced into a cell in vivo by local injection of or by other appropriate viral or non-viral delivery vectors. Hefti, *Neurobiology,* 25:1418-1435 (1994). For example, the siRNA molecule may be contained in an adeno-associated virus (AAV) vector for delivery to the targeted cells (e.g., Johnson, International Publication No. WO95/34670; International Application No. PCT/US95/07178). The recombinant AAV genome typically contains AAV inverted terminal repeats flanking the siRNA sequence operably linked to functional promoter and polyadenylation sequences. Alternative suitable viral vectors include, but are not limited to, retrovirus, adenovirus, herpes simplex virus, lentivirus, hepatitis virus, parvovirus, papovavirus, poxvirus, alphavirus, coronavirus, rhabdovirus, paramyxovirus, and papilloma virus vectors.

Nonviral delivery methods include, but are not limited to, liposome-mediated transfer, naked DNA delivery (direct injection), receptor-mediated transfer (ligand-DNA complex), electroporation, calcium phosphate precipitation, and microparticle bombardment (e.g., gene gun). Methods of introducing the siRNA molecules may also include the use of inducible promoters, tissue-specific enhancer-promoters, DNA sequences designed for site-specific integration, DNA sequences capable of providing a selective advantage over the parent cell, labels to identify transformed cells, negative selection systems and expression control systems (safety measures), cell-specific binding agents (for cell targeting), cell-specific internalization factors, and transcription factors to enhance expression by a vector as well as methods of vector manufacture.

The preferred siRNA molecule is 19-25 base pairs in length, most preferably 21-23 base pairs, and is complementary to the target gene sequence. The siRNA molecule preferably has two adenines at its 5' end, but may not be an absolute requirement. The siRNA sequences that contain 30-50% guanine-cytosine content are known to be more effective than sequences with a higher guanine-cytosine content. Therefore, siRNA sequence with 30-50% are preferable, while sequences with 40-50% are more preferable. The preferred siRNA sequence also should not contain stretches of 4 or more thymidines or adenines.

The present specification provides details of studies performed with siRNAs designed to target the TGFβ type II receptor (TGFβII) gene. The target sequence selected should not be highly structured or bound by regulatory proteins. Preferably, the siRNA molecules of the invention should be directed to different positions within the target gene sequences. For example, siRNA target sequences NK1, NK2, SS1 and SS2 (SEQ ID NO: 1-4) are directed to different portions of the TGFβRII gene. In particular nucleotides NK1 spans nucleotides 529-612, NK2 spans nucleotides 1113-1133, SS1 spans nucleotides 1253-1273 and SS2 spans nucleotides 948-969 of the TGFβRII gene. Additional siRNA target sequences that may be effective for suppressing TGFβRII gene expression are set out in Table 1 below. These sequences were derived by analyzing the human TGFβRII sequence (M85079) using the publicly available siRNA Target Finder program at the Ambion, Inc. web site. The sequences were screened by BLAST searching the Genbank database for homologous sequences. Any sequence containing more than 16 nucleotides match to a non-TGFβRII sequence were eliminated from further consideration.

Sequences with a GC content between 30-50% were further analyzed. Those sequences containing four consecutive A, C, G or T bases were eliminated. This analysis identified an additional 49 siRNA molecules that are contemplated to be effective in inhibiting TGFβRII gene. These sequences are shown in FIG. 3. The siRNA molecules that contain up to 2 mismatches are effective in inhibiting TGFβRII expression. The effectiveness of the siRNA containing mismatches may be dependent on their position in the sequence. Thus, it is likely that other siRNA sequences may be derived from the 4 already tested (NK1, NK2, SS1 and SS2) and those indicated in FIG. 3.

The present specification provides details of studies performed with siRNAs designed to target the TGFβ type II receptor (TGFβRII) gene. In cultured human corneal fibroblasts, the siRNAs effectively suppressed gene expression of the receptor, reduced TGFβ-mediated matrix deposition and retarded cell migration. In addition, the data presented herein shows in an in vivo model that siRNAs specific for TGFβRII can reduce inflammation and regulate wound repair in the conjunctiva of mouse eyes. The siRNA molecules of the present invention also effectively suppress TGFβRII gene expression in human umbilical vein endothelial cells. siRNAs specific to human TGFβRII can inhibit the receptor expression in cultured human corneal fibroblasts as shown by immunofluorescence, Western blotting and real time PCR analyses. Four concentrations of siRNAs ranging from 25 to 200 nM and four time points from 16 to 72 hours were tested. The inhibitory response is both dose and time dependent. Specificity of the siRNAs for the TGFβRII has also been established. All four siRNAs tested were found to be efficacious, although two of them showed greater effect. Given the teachings provided herein, one of skill in the art would expect that other siRNAs deduced from the cDNA sequence of human TGFβRII also will be as effective.

Assays to Test Efficacy of siRNA Specific to Human TGFβ Type II Receptor in vitro Models Corneal fibroblasts constitutively express TGFβ. (Song et al., *J. Cell. Biochem.* 77, 186-199 (2000), Imanishi et al., *Prog. Retin. Eye Res.* 19, 113-129 (2000)). The effects of siRNAs in blocking autocrine TGFβ signaling in corneal fibroblasts was examined and are described herein. The functional roles of the siRNAs are thus well established in this in vitro culture model.

TGFβ has been shown to enhance the expression of matrix molecules such as fibronectin and collagen type I (Song et al., *J. Cell. Biochem.* 77, 186-199 (2000), Massague, *Annu. Rev. Cell Biol.* 6, 597-641 (1990)) and to facilitate migration of corneal fibroblasts, (Imanishi et al., *Prog. Retin. Eye Res.* 19, 113-129 (2000), Andersen et al, *Curr. Eye Res.* 16, 605-613 (1997)), and the steps involved in the complex wound repair process. (Clark, *Physiology, Biochemistry and Molecular Biology of the Skin,* Oxford University Press. P. 576-601, 1997) As has been demonstrated in hepatic stellate cells with antisense RNA complementary to TGFβ1, (Arias et al., *Cell Growth Differ.* 13, 265-273 (2002)) diminished receptor level and blockade of receptor binding for TGFβ caused a reduction in the secreted fibronectin level and its incorporation into the matrix. Corneal fibroblast migration is also markedly retarded.

Given the teachings of the present invention, those of skill in the art are instructed to produce siRNA molecules discussed herein and employ such molecules in in vitro assays to assess the effects of such siRNA molecules on migration of corneal fibroblasts, the expression of fibronectin, and/or the expression of collagen type I. Any decrease or diminution of the level of migration of corneal fibroblasts, the level of expression and/or secretion of either fibronectin or collagen type I will be indicative of the given siRNA molecule being effective for use as a therapeutic agent in accordance with the present invention.

Mouse Models

The therapeutic effects of the TGFβ specific siRNA molecules are also demonstrated in a conjunctival scarring mouse model. The model was similar to that described previously by Reichel et al. (*Br. J. Opthalmol.* 82, 1072-1077 (1998)). However, instead of injecting only PBS into the subconjunctival space, the injected PBS was mixed with latex beads to have an improved mouse model with augmented inflammatory and scarring response. siRNA at 200 nM clearly showed its effectiveness in reducing the inflammatory and fibrotic response in this new mouse model. Those of skill in the art could repeat these model studies with any other TGFβ specific siRNA molecule. Any other molecule that reduces the inflammatory or fibrotic response in this mouse model is contemplated to be a useful siRNA molecule of the invention.

Cell Growth Assays

TGFβ is known to stimulate fibroblast proliferation and inhibit proliferation of epithelial cells, in particular tumor cells. Therefore, measuring the effect of siRNA on TGFβ-induced fibroblast proliferation or epithelial cell growth inhibition is a method for evaluating the effectiveness of the siRNA molecules.

Cell growth may be monitored by measuring DNA synthesis. DNA synthesis may be measured using [$^3$H]-thymidine incorporation in cells as described in Lee et al., (*Endocrinology* 136:796-803, (1995)). Cells are seeded at approximately $2 \times 10^4$ per well (24-well plate) and are incubated for 22 hours in 1 ml culture medium with or without 1% FBS and containing TGFβ at selected concentrations. Then 2 mCi per well [$^3$H]-thymidine is added, subsequently incubation continues for 4 hours, and radioactivity is counted with a scintillation counter.

Cell proliferation can be measured by cell counting. Cells are seeded (24-well plates) in culture medium with or without 1% FBS and medium is changed every other day. At the end of a 4-day culture, cells are trypsinized and counted in a Coulter counter.

TGFβRII Activation Assays

The use of the p3TP-lux construct allows for evaluation of activation of the TGFβ type II receptor. Cells are seeded at $1 \times 10^5$ cells per well in 6-well plates and are transiently transfected with the plasmid p3TP-Lux using lipofection according to manufacturer's instructions (Life Technologies, Gaithersburg, Md.). p3TP-Lux contains three 12-O-tetradecanoylphorbol-13-acetate-responsive elements from the human collagen gene and one TGFβ-responsive element from the human plasminogen activator inhibitor-1 (PAI-1) promoter linked to the luciferase reporter gene (Wrana et al., *Cell* 71: 1003-14, (1996)). Cells are incubated with 1 μg/ml p3TP-Lux and 12 μg/ml Lipofectamine for 24 hours. Subsequently, cells are treated with 5 ng/ml TGFβ in RPMI for 24 hours and lysed with extraction buffer (100 mM potassium phosphate, pH 7.5, 1% Triton X-100, 100 mg/ml bovine serum albumin, 2.5 mM phenylmethylsulfonylfluoride, 1 mM dithiothreitol). Lysates are diluted into reaction buffer (75 mM MgCl2, 1 M glycylglycine, pH 7.8, 100 mg/ml bovine serum albumin, 60 mg/ml ATP) and are assayed for luciferase activity using a luminometer.

Use of this assay allows one to evaluate the effectiveness of the siRNA on TGFβRII activity. An effective siRNA molecule of the present invention will inhibit the amount of signaling through the TGFβRII receptor as it will reduce the number of receptors available for signaling. Preferably, the effective siRNA molecule will inhibit signaling through TGFβRII by at least 20%, or more preferably by at least 25%, 30%, 35%, 40% or 45%. It is highly preferable that the effective siRNA molecule inhibit signaling through the TGFβRII by at least 50%, 55%, 60%, 65%, 70, 75% or more.

Chemotaxis Assays

TGFβ is a cytokine and those of skill in the art monitor the activity of such agents through well known chemotaxis assays. Exemplary chemotaxis assays that may be performed are described in Martinet et al., *J. Immunol. Meth.*, 174:209, 1994 and Keller et al., *J. Immunol. Meth.*, 1:165, 1972. Briefly, 20 ml of peripheral blood is collected from health volunteers in 10 ml heparinized tubes. Blood is diluted 1:1 and then under laid with 10 ml of Histopaque (Sigma). After centrifugation at 400 g for 25 minutes, cells at the interface are collected and washed twice in PBS. Cells are resuspended in DMEM (Life Technologies, Gaithersburg, Md.) with 100 U/ml penicillin and 100 μg/ml streptomycin (tissue culture antibiotics, Life Technologies) at 106/ml. Sterile bovine serum albumin (Sigma) is added to final concentration of 0.2 mg/ml.

100 μl of this cell suspension is added to each transwell insert (Costar). DMEM with antibiotics and 0.2% BSA with or without siRNA molecules is added to the lower wells in the 24 well plate. Transwell inserts are placed into the lower walls, and incubated at 37N C for 90 minutes. At the completion of the incubation period inserts are removed and the adherent cells are removed. The entire insert is then stained with Wright-Giemsa. Cells adherent to the lower surface of the insert and those that migrated to the lower well are counted under microscope, and added together to obtain a total number of migrating cells.

Assay of Chemoattractant and Cell-Activation Properties

The effects of siRNA directed to TGFβRII upon human monocytes/macrophages or human neutrophils may be evaluated, e.g., by methods described by Devi et al., *J. Immunol.*, 153:5376-5383 (1995) for evaluating murine TCA3-induced activation of neutrophils and macrophages. Indices of activation measured in such studies include increased adhesion to fibrinogen due to integrin activation, chemotaxis, induction of reactive nitrogen intermediates, respiratory burst (superoxide and hydrogen peroxide production), and exocytosis of lysozyme and elastase in the presence of cytochalasin B.

As discussed by Devi et al., these activities correlate to several stages of the leukocyte response to inflammation. This leukocyte response, reviewed by Springer, *Cell*, 76:301-314 (1994), involves adherence of leukocytes to endothelial cells of blood vessels, migration through the endothelial layer, chemotaxis toward a source of chemokines, and site-specific release of inflammatory mediators.

Assays of Effect on Myeloid Progenitor Cells

The inhibition of TGFβ-induced suppression of hematopoiesis may be tested in assays of stem/progenitor cell function and number, including LTC-IC, CFU-GEMM, CFU-GM, BFU-E. These assays are well known to those of skill in the art and are relatively straightforward to set up as described in for example Broxmeyer et al., *Blood*, 76:1110 (1990). Briefly, bone marrow cells are collected from human donors after obtaining informed consent. Low density human bone marrow cells at $5 \times 10^4$/ml are plated in 1% methylcellulose in Iscove's Modified Essential Medium (Biowhitaker, Walkersville, Md.) supplemented with 30% FCS (Hyclone), recombinant human erythropoietin (EPO, 1 U/ml, Amgen, Thousand Oaks, Calif.), recombinant human interleukin-3 (IL-3, 100 U/ml, Immunex, Seattle, Wash.), and recombinant human stem cell factor (SCF, 50 ng/ml, Amgen) for colony forming unit granulocyte/macrophage (CFU-GM), colony forming unit granulocyte/erythrocyte/macrophage/megakaryocyte (CFU-GEMM) or blast forming unit-erythrocyte (BFU-E) analysis. Cultures are incubated at 5% CO2 and low oxygen tension (5%) for 14 days, and then scored for colony formation using an inverted microscope in a blinded fashion.

Assays for Effects on Myeloid Cell Lines

The effect of siRNA on TGFβ-induced inhibition of myeloid cell proliferation also may be a useful test of functional activity of the siRNA molecules. Such a functional assay may be assessed using the human myeloid cell lines TF-1 and MO7E (Avanzi et al., *Brit. J. Haematol.*, 69:359; 1988), which require GM-CSF and SCF for maximal proliferation. The cytokine-dependent primitive acute myeloid leukemia cell lines TF-1 and MO7E may be cultured in RPMI 1640 (Life Technologies, Gaithersburg, Md.) plus 10% FCS (Hyclone) and 100 U/ml penicillin and 100 µg/ml streptomycin (tissue culture antibiotics, Life Technologies, Gaithersburg, Md.). This media is supplemented with granulocyte-macrophage colony stimulating factor (GM-CSF, 100 U/ml, Immunex, Seattle, Wash.) and stem cell factor (SCF, 50 ng/ml, Amgen, Thousand Oaks, Calif.) to promote normal log phase growth.

Assays for Effect on Chronic Myelogenous Leukemia Progenitors

The effect of siRNA on TGFβ-induced inhibition of progenitor proliferation in chronic myelogenous leukemia (CML) may be evaluated using colony formation assays as described in Hromas et al., *Blood*, 89:3315-3322 (1997). Briefly, bone marrow cells are collected from six CML patients in chronic phase. Low density marrow cells at for example, 5×104 cells/mL are plated in 1% methylcellulose in Iscove's modified Dulbecco's medium supplemented with 30% fetal calf serum, 1 U/mL human erythropoietin (Epogen®, Amgen), 100 U/mL human interleukin-3 (Genetics Institute) and 50 ng/mL human stem cell factor (Amgen), in the presence or absence of an appropriate concentration of TGFβ (e.g. 100 ng/ml) alone or in combination with other chemokines such as EXODUS, MIP-1α and the like.

Cultures are incubated at 5% CO2 and low (5%) oxygen tension for 14 days, and then scored using an inverted microscope for CFU-GM, CFU-GEMM and BFU-E. Colony counts for cultures treated with chemokines are compared to colony counts of the control cultures and were expressed as a percentage of control CFU or BFU.

As stated earlier, the assays described above are intended to exemplify the types of assays that may be conducted to determine the in vitro and in vivo effects of the siRNA molecules of the present invention. These are by no means the only assays known to be used for determine TGFβ activity. Those of skill in the art will know of other assays that may be substituted for these described above but nonetheless measure similar parameters of function and activity.

Angiogenesis Assays

The effect of siRNA molecules on angiogenesis may be monitored using the following assays. Angiogenesis is the multistep process of new capillary formation originating from sprouting of endothelial cells from the wall of an existing small blood vessel. In order for new capillary tubes to form, endothelial cells must elongate and migrate.

A tube formation assay may be utilized to determine if the siRNA molecules targeting TGFβRII inhibit tube formation in endothelial cells such as HUVEC cells. For example endothelial tube formation assays may be carried out in vitro using Matrigel. When endothelial cells are plated on BD Matrigel™ (BD Biosciences), the cells stop proliferating, and display high motility and cell-cell communication. Furthermore, within 24 hours, the cells align and form a three-dimensional network of capillary tubes that has been proposed as a model of endothelial cell differentiation as well as one of the final steps of the angiogenic cascade.

A 24-well tissue culture plate is coated with 500 µl of the Matrigel Matrix with reduced growth factors and allowed to gel thoroughly by incubating at 37° C. for at least 30 minutes. After the Matrigel forms a gel, endothelial cells such as bovine aortic endothelial cells (BAEC) or human umbilical vein endothelial cells (HUVEC) are washed and seeded on Matrigel coated wells. The cells are treated with TGFβ in the presence and absence of siRNA molecules targeted to TGFβRII, To view tube formation, cells are treated with 1 mM Calcein AM (Molecular Probes) diluted at 1:2000 in media, incubated in the dark for at least 15 minutes, and subsequently washed with media+10% FBS.

Other assays to evaluate the effect of siRNA molecules on TGFβ-induced angiogeneis include endothelial cell proliferation assays and endothelial cell migration assays. In addition, alterations in endothelial cells occur during angiogenesis as vessels invade tumors, and have effects on endothelial cell morphology and function. Endothelial cell morphology may be evaluated using immunohistochemistry or electron microscopy to view endothelial cell sprouting, migration, and proliferation.

The Chicken Chorioallantoic Membrane (CAM) assay is also a well known method of evaluating angiogenesis. The developing chicken embryo is surrounded by a chorioallantoicmembrane, which becomes vascularized as the embryo develops. Tissue grafts are placed on the CAM through a window made in the eggshell. This causes a typical radial rearrangement of vessels towards, and a clear increase of vessels around the graft within four days after implantation. Blood vessels entering the graft are counted under a stereomicroscope. To assess the anti-angiogenic or angiogenic activity of the siRNA molecules, the compounds are either prepared in slow release polymer pellets, absorbed by gelatin sponges or air-dried on plastic discs and then implanted onto the CAM. In the CAM assay, siRNA of the present invention that lead to the regression of newly developed CAM vasculature are determined to be effective inhibitors of TGFβ-induced angiogenesis.

The effect of the siRNA molecules of the present invention on TGFβ-induced angiogeneis may also be measured in the mouse cornea using the micropocket assay. The mouse cornea presents an in vivo avascular site. This makes it a very good model for studying angiogenesis, as the growth of new blood vessels easily can be studied under microscope. Any vessels penetrating from the limbus into the corneal stroma can be identified as newly formed. To induce an angiogenic response, slow release polymer pellets (i.e. poly-2-hydroxy-ethyl-methacrylate (hydron) or ethylene-vinyl acetate copolymer (ELVAX)), containing an TGFβ is implanted in "pockets" created in the corneal stroma of a mouse. After 4-6 days, new vessel growth occurs. The vascular response can be quantified by computer image analysis after perfusion of the cornea with India ink. The blood vessels in this model can also be studied ultrastructurally by electron microscope, or by the use of immunohistochemistry.

Pharmaceutical Compositions

Where clinical applications are contemplated, it will be necessary to prepare the viral expression vectors, nucleic acids and other compositions identified by the present invention as pharmaceutical compositions, i.e., in a form appropriate for in vivo applications. Generally, this will entail preparing compositions that are essentially free of pyrogens, as well as other impurities that could be harmful to humans or animals. In preferred embodiments, the present invention contemplates pharmaceutical compositions containing siRNA molecules described as the present invention.

The active compositions of the present invention include classic pharmaceutical preparations. Administration of these compositions according to the present invention will be via any common route so long as the target tissue is available via that route. The pharmaceutical compositions may be introduced into the subject by any conventional method, e.g., by intravenous, intradermal, intramuscular, intramammary, intraperitoneal, intrathecal, intraocular, retrobulbar, intrapulmonary (e.g., term release); by oral, sublingual, nasal, anal, vaginal, or transdermal delivery, or by surgical implantation at a particular site, e.g., embedded under the splenic capsule, brain, or in the cornea. The treatment may consist of a single dose or a plurality of doses over a period of time.

The active compounds may be prepared for administration as solutions of free base or pharmacologically acceptable salts in water suitably mixed with a surfactant, such as hydroxypropylcellulose. Dispersions also can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like that do not produce adverse, allergic, or other untoward reactions when administered to an animal or human. The use of such media and agents for pharmaceutical active substances is well known in the art. Except insofar as any conventional media or agent is incompatible with the active ingredient, its use in the therapeutic compositions is contemplated. Supplementary active ingredients also can be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration.

"Unit dose" is defined as a discrete amount of a therapeutic composition dispersed in a suitable carrier. For example, where siRNA molecules are being administered parenterally, siRNA compositions are generally injected in doses ranging from 1 mg/kg to 100 mg/kg body weight/day, preferably at doses ranging from 0.1 mg/kg to about 50 mg/kg body weight/day. Parenteral administration may be carried out with an initial bolus followed by continuous infusion to maintain therapeutic circulating levels of drug product. Those of ordinary skill in the art will readily optimize effective dosages and administration regimens as determined by good medical practice and the clinical condition of the individual patient.

The frequency of dosing will depend on the pharmacokinetic parameters of the agents and the routes of administration. The optimal pharmaceutical formulation will be determined by one of skill in the art depending on the route of administration and the desired dosage. See for example Remington's Pharmaceutical Sciences, 18th Ed. (1990, Mack Publ. Co, Easton Pa. 18042) pp 1435-1712, incorporated herein by reference. Such formulations may influence the physical state, stability, rate of in vivo release and rate of in vivo clearance of the administered agents. Depending on the route of administration, a suitable dose may be calculated according to body weight, body surface areas or organ size. Further refinement of the calculations necessary to determine the appropriate treatment dose is routinely made by those of ordinary skill in the art without undue experimentation, especially in light of the dosage information and assays disclosed herein as well as the pharmacokinetic data observed in animals or human clinical trials.

Appropriate dosages may be ascertained through the use of established assays for determining blood levels in conjunction with relevant dose-response data. The final dosage regimen will be determined by the attending physician, considering factors which modify the action of drugs, e.g., the drug's specific activity, severity of the damage and the responsiveness of the patient, the age, condition, body weight, sex and diet of the patient, the severity of any infection, time of administration and other clinical factors. As studies are conducted, further information will emerge regarding appropriate dosage levels and duration of treatment for specific diseases and conditions.

In gene therapy embodiments employing viral delivery, the unit dose may be calculated in terms of the dose of viral particles being administered. Viral doses include a particular number of virus particles or plaque forming units (pfu). For embodiments involving adenovirus, particular unit doses include 103, 104, 105, 106, 107, 108, 109, 1010, 1011, 1012, 1013 or 1014 pfu. Particle doses may be somewhat higher (10 to 100-fold) due to the presence of infection defective particles.

It will be appreciated that the pharmaceutical compositions and treatment methods of the invention may be useful in fields of human medicine and veterinary medicine. Thus the subject to be treated may be a mammal, preferably human or other animal. For veterinary purposes, subjects include for example, farm animals including cows, sheep, pigs, horses and goats, companion animals such as dogs and cats, exotic and/or zoo animals, laboratory animals including mice rats, rabbits, guinea pigs and hamsters; and poultry such as chickens, turkey ducks and geese.

Combined Therapy

In addition to therapies based solely on the delivery of siRNA molecules and related composition, combination therapy is specifically contemplated. In the context of the present invention, it is contemplated that siRNA methods could be used similarly in conjunction with other agents for promoting wound-healing, reducing scarring, inhibiting angiogenesis, or those used in the therapy of the disorders enumerated herein. It is also contemplated that the siRNA molecules directed to TGFβRII could be used in conjunction with other siRNA molecules that promote wound healing, reducing scarring, inhibiting angiogenesis or those used in the therapy of the disorders described herein.

To achieve the appropriate therapeutic outcome, be it a decrease in scarring, decrease in fibrogen accumulation, reduction in angiogenesis or any other use for the siRNA molecules discussed herein, using the methods and compositions of the present invention, one would generally contact a "target" cell with a siRNA expression construct and at least one other therapeutic agent (second therapeutic agent). These compositions would be provided in a combined amount effective to produce the desired therapeutic outcome. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second therapeutic agent.

Alternatively, the siRNA treatment may precede or follow the other agent treatment by intervals ranging from minutes to weeks. In embodiments where the second therapeutic agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

Local delivery of siRNA expression constructs or sequences to patients may be a very efficient method for delivering the siRNA molecules to counteract a clinical disease. Similarly, the second therapeutic agent may be directed to a particular, affected region of the subject's body. Alternatively, systemic delivery of expression construct and/or the second therapeutic agent may be appropriate in certain circumstances.

Other antiproliferative and anti-angiogenic compositions which may be effective include in combination treatments with the siRNA molecules of the present invention include anti-cancer drugs mitomycin-C and 5-fluorouracil, *agaricus bisporus* lectin, metallocomplexes such as zinc-desferrioxaminde or gallium-desferrioxamine, methyl xanthine derivatives such as pentoxifylline, collagen-based sealants such as GE Amidon Oxyde. In addition, agents that inhibit VEGF, fibroblast growth factors, connective tissue growth factors and matrix metalloproteinase inhibitors such as ilomastat are contemplated as second therapeutic agents for use with the siRNA molecules of the present invention. Such inhibitors include siRNA molecules that target VEGF, fibroblast growth factors, connective tissue growth factors or the respective receptors for these growth factors and matrix metalloproteinases.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Materials & Methods

Human Corneal Fibroblast Cultures

Normal human corneas from donors aged 13, 29, 34, 45, and 47 years were obtained from either the Illinois Eye Bank (Chicago, Ill.) or the National Disease Research Interchange (Philadelphia, Pa.). The procurement of tissue was approved by the IRB Committee at the University of Illinois at Chicago in compliance with the declaration of Helsinki. The endothelial and epithelial layers were removed from the corneas and the stroma was used as explants to initiate corneal fibroblast cultures. The cells were maintained in Dulbecco's modified Eagle's minimum essential medium (MEM) supplemented with glutamine, 10% fetal calf serum, 5% calf serum, nonessential and essential amino acids and antibiotics as previously described in Yue and Blum. (Vision Res. 21, 41-43 (1981)) Third- to fifth-passaged cells were used for the study.

TGFβII Receptor siRNA sequences

Four sequences for the TGFβII receptor siRNA were derived from the human TGFβII receptor sequence (Genbank Accession Number: M85079). The siRNAs were custom synthesized and purified by Dharmacon Research (Lafayette, Colo.).

The target sequences (5' to 3') were as follows, with the position of the first nucleotide in the human TGFβII receptor sequence shown in brackets:

```
NK1:  (529)   AATCCTGCATGAGCAACTGCA   (SEQ ID NO: 1)
NK2:  (1113)  AAGGCCAAGCTGAAGCAGAAC   (SEQ ID NO: 2)
SS1:  (1253)  AAGCATGAGAACATACTCCAG   (SEQ ID NO: 3)
SS2:  (948)   AAGACGCGGAAGCTCATGGAG   (SEQ ID NO: 4)
```

RNA of a scrambled sequence was used as a control.

Transfection of siRNA Duplexes

Normal human corneal fibroblasts were plated at 50-70% confluence onto Lab-Tek 4- or 8-well chamber slides, coverslips, or 6-well plates the day prior to the transfection. Transfection complexes were prepared by adding 2 μl of TransIT-TKO reagent (Takara Mirus Corporation, Madison, Wis.) to 50 μl of serum-free media, vortexing and incubating the mixture at room temperature for 10 min. To the mixture, anti-TGFβII receptor siRNA duplex (25, 50, 100, or 200 nM final concentration) was added. The solution was further mixed by gently pipeting and was incubated for another 20 minutes. The final mixture was then added dropwise to the cells in complete media. After gentle rocking, the cells were incubated at 37° C. for 16, 24, 48, or 72 hours before assaying for gene expression. As controls, corneal fibroblasts were either untreated or treated only with the transfection reagent. Nonspecific scrambled siRNA duplex (Dharmacon; 100 and 200 mM) was also used in place of the TGFβRII specific siRNAs.

Immunofluorescence

At selected time points after siRNA transfection, cells in coverslips or 8-well chamber slides (Nalge Nunc International, Naperville, Ill.) were fixed with 2% formaldehyde solution and permeabilized with 0.1% Triton-X100 in PBS. Cells were blocked for 45 minutes at room temperature in 10% heat-inactivated normal goat serum (Colorado Serum Company, Denver, Colo.), and incubated with a rabbit anti-TGFβII receptor antibody (1:100, Santa Cruz Biologicals, Santa Cruz, Calif., SC1700) for 60 min. Following washes, a goat FITC-anti-rabbit (Southern Biotechnology) at 1:200 was applied for a 60-minutes incubation. The nuclei of the cells were counterstained with DAPI (4',6'-diamidino-2-phenylindole dihydrochloride). The slides were examined by epifluorescence under a Zeiss Axiovert fluorescence microscope (Carl Zeiss, Jena, Germany).

For fibronectin staining, cells on Lab-Tek 4-well glass chamber slides were fixed 48 hours after transfection in ice cold methanol. Immunofluorescence was performed using a rabbit anti-human fibronectin (1:100, BD Science, Lexington, Ky.) as the primary antibody and FITC-conjugated goat anti-rabbit IgG (1:100, Jackson ImmunoResearch, West Grove, Pa.) as the secondary antibody. The slides were mounted in Vectashield (Vector Laboratories, Burlingame, Calif.) with DAPI. The staining was examined under a Zeiss 100M microscope.

Western Blotting

After siRNA transfection, the media were removed and corneal fibroblasts in 6-well plates were harvested. Cells were lysed in a Triton buffer, followed by addition of sodium dodecyl sulfate (SDS) sample buffer. Protein samples were separated on a 10% SDS-polyacrylamide gel, transferred to nitrocellulose membranes and blocked with BLOTTO. Subsequently, blot was incubated with rabbit anti-TGFβII receptor at 1:200 dilution (of course, other dilutions e.g., 1:2000, and dilutions in between these figures also could be used) and horseradish peroxidase (HRP)-conjugated goat anti-rabbit IgG (Jackson ImmunoResearch). Signals were detected by chemiluminescence.

For fibronectin study, corneal fibroblasts after transfection were incubated with serum-free MEM for 24 hours. The media were collected and the cells were lysed on ice in 10 mM Tris-HCl (pH 8.0), 150 mM NaCl, 0.5% NP-40, 2 mM phenylmethylsulfonyl fluoride, and 1× cocktail protease inhibitors (Roche). Cellular debris was pelleted, and the proteins in the lysate were quantified by Bradford protein assay. After adjusting the protein amounts, equal aliquots of media samples were resolved on 10% SDS-polyacrylamide gels under reducing conditions. The proteins were electroblotted onto nitrocellulose membranes. After blocking with 5% nonfat dry milk, the membranes were incubated with rabbit anti-human fibronectin (1:5000) and HRP-goat anti-rabbit IgG (1:10,000). Protein bands were detected using SuperSignal Substrate from Pierce (Rockford, Ill.). Densitometric analysis was performed to measure the intensity of the fibronectin bands with the use of 1D Image Analysis software (Kodak Digital Imaging, Eastman Kodak Company, New Haven, Conn.).

Real Time PCR

Total RNA was extracted with Trizol from cells treated for 24, 48, and 72 hours with scrambled, NK1, or SS1 siRNA. Real time PCR was performed according to methods known to those of skill in the art.

Cell Migration Assay

A wound scratch assay was used to assess cell migration. Forty eight hours after transfection, corneal fibroblasts in 24-well plates were scratched with a sterile P20 pipette tip as previously described in Mostafavi-Pour et al., J. Cell Biol. 161: 155-167 (2003). The ability of cells to migrate into the wound was examined under phase contrast microscopy 7 hours after wounding. To quantify the extent of migration, total area of the wound in each 10× field and the areas devoid of cells within the wound were measured with the use of the Image Processing Tool Kit version 3.0 (an Adobe Photoshop 7.1 plugin software, Reindeer Graphics, Inc., Asheville, N.C.). A total of 10 fields were analyzed and the mean percentage of areas covered by the migratory cells in each specimen was calculated. Student's t tests were used for statistical evaluation. All experiments were repeated at least 3 times.

Mouse Model of Conjunctival Scarring

All experiments were performed using 6 week old C57BL6 mice. Treatment of the animals was conformed to the ARVO Statement for the Use of Animals in Ophthalmic and Vision Research. Mice underwent general anesthesia with intraperitoneal injections (pentobarbital, 0.1 ml/10 g body weight).

Surgery was performed as reported previously with modifications. (Reichel et al. Br. J. Opthalmol. 82, 1072-1077 (1998)). A blunt dissection of the temporal subconjunctival space was performed using 1 ml syringe and 30 gauge needle by injecting of sterile PBS (pH 7.4) containing latex beads (1.053 μm diameter, 300 μg/ml, Polysciences, Warrington, Pa.) with transfection reagent mixed with 200 nM NK1, SS1, or scrambled missense oligonucleotide. One eye of each mouse was treated with HK1 or SS1, and the contralateral eye was treated with the scrambled siRNA in a double masked manner. Eyes in other mice were either left untreated or injected with PBS and latex beads alone to serve as controls. Mice were sacrificed by cervical dislocation 2, 7, and 14 days after surgery. For each treatment/time point, three mice were used.

Eyes enucleated eyes were fixed at room temperature with 10% buffered formalin for 24 hours, and were processed for paraffin sections. Five-μm-thick paraffin-embedded sections were deparaffinized, rehydrated, and stained with hematoxylin and eosin (H & E) to assess the inflammatory reaction and picrocirius red to demonstrate collagen deposition.

Example 2

Suppression of TGFβII Receptor Protein and mRNA Expression

Human corneal fibroblasts were transfected with all four exemplary siRNAs designed using the TransIT-TKO reagent. The cellular uptake of oligonucleotides was demonstrated by fluorescence microscopy using the Cy3-labeled luciferase. The transfection seemed to be extremely efficient, with more than 90% of the cells displaying red fluorescence. Little cytotoxicity of the transfection reagent or the siRNAs was observed.

Immunofluorescence analyses showed that TGFβRII was distributed diffusely in the cytoplasm of untreated control corneal fibroblasts (FIG. 1, row 1). When treated with 100 nM of SS1 siRNA for 48 h, the TGFβRII staining intensity was dramatically reduced (FIG. 1, rows 3 and 4). At 100 nM, NK1, NK2 and SS2 siRNAs also suppressed the TGFβRII intensity. While not evident at the lowest concentration (25 nM) and the shortest time point (16 h) tested, the inhibiting effects, to varying degrees, were also observed for all four siRNAs tested with other concentrations (50 and 200 nM) and time points (24 and 72 h). Overall, NK1 and SS1 appeared to result in a greater inhibition than the others. Cells treated with scrambled siRNA (FIG. 1, row 2) showed a similar intensity and pattern as the untreated control cells, demonstrating the specificity of NK1 and SS1 effects.

Western blotting (FIG. 2) yielded a 73-75 kDa band (a diffuse band as the receptor is a glycoprotein) immunoreactive to anti-TGFβRII in the vehicle-treated control and scrambled siRNA-transfected samples. There was no discernible difference in the TGFβRII protein level at the 16 hours time point except for the cells treated with SS1 (lane 6) where a reduction was seen. At 48 h, both NK1 (lanes 9 and 10) and SS1 (lanes 11 and 12) siRNAs showed a marked decrease in signal intensity for TGFβII receptor compared to control cells (lane 8). A densitometric analysis suggests a 70-85% reduction of the TGFβRII in the siRNA treated immunoblots. NK1 siRNA appeared to be more effective than SS1 in reducing the TGFβRII expression at this time point at both 50 and 100 nM siRNA concentrations.

Figure 2:
FIG. 2. Suppression of TGFβI type II receptor protein expression by siRNA in corneal fibroblasts. Lysates from human corneal fibroblasts treated with different concentrations of TGFβRII receptor siRNA or control, scrambled siRNA for 16 (top panel) or 48 hours (bottom panel) were separated on 10% SDS-polyacrylamide gels and immunoblotted with a TGFβRII receptor antibody. Lane 1 contains lysate from cells incubated only with TransIT-TKO reagent (no siRNA). Lanes 2 and 8 contain lysates from cells treated with 100 nM scrambled siRNA. Lanes 3, 4, 9 and 10 contain lysates of cells treated with NK1 siRNA at a final concentration of 50 (lanes 3 and 9) or 100 nM (lanes 4 and 10). Lanes 5, 6, 11 and 12 contain lysates of cells treated with SS1 siRNA at 50 (lanes 5 and 11) or 100 nM (lanes 6 and 12). In lane 7, the TGFβRII receptor antibody was preincubated with antigenic peptide before probing the normal cell lysate. Similar amounts of total protein were loaded in each lane.

When the TGFβII receptor antibody was preincubated with the antigenic peptide before probing, the immunoreactive band disappeared (FIG. 2, lane 7). The lack of a signal in this lane demonstrates the specificity of the antibody. The turnover rate varies with the presence of ligand binding and with the cell type used. The half life of TGFβRII receptor varied from 2-6 hours. TGFβII receptor transcript was examined by real time PCR and it was seen that the siRNA compositions significantly changed the level of receptor mRNA.

Example 3

Reduction of Fibronectin Assembly and Secreted Fibronectin by siRNAs

Using immunofluorescence, it was demonstrated that untreated control corneal fibroblasts exhibited robust fibronectin deposition and a dense fibrillar network over cells. A similar pattern was also observed in cells treated with scrambled siRNA. In these analyses immunofluorescence of untreated fibroblasts or fibroblasts treated for 48 hours with scrambled siRNA, 100 or 200 nM NK1, or 100 or 200 nM SS1 was performed to visualize fibronectin matrix. Staining of nuclei was performed using DAPI stain. These studies showed that fibronectin deposition was markedly reduced in corneal fibroblasts 48 hours after transfection with both 100 and 200 nM of NK1 and SS1 siRNAs. The nuclei were counterstained by DAPI. The cell density was similar in the various specimens and thus the decreased fibronectin assembly was not related to a decrease in cell number.

The effects of the siRNAs on the fibronectin fibrillogenesis also was examined through observing changes in fibronectin secretion. Corneal fibroblasts, 48 hours after transfection, were incubated in serum-free medium for 24 hours. Proteins collected in the media were subjected to Western blotting. A 220-Kda fibronectin band was observed in all samples. Consistent with the immunofluorescence data, treatment with 100 and 200 nM NK1 and SS1 resulted in a decreased level of fibronectin secreted into the culture media. The two siRNAs were equally effective, eliciting greater effect with 200 nM than 100 nM.

Example 4

Retardation of Cell Migration by siRNAs

Wound scratch assays indicated that corneal fibroblasts were able to move into the wounded area. Within 7 hours, untreated control and scrambled RNA-transfected cells filled most of the pipette tip-generated wound, covering 83.0±2.2% and 80.4±2.6% of the area, respectively. By contrast, the wound area covered by 100 and 200 nM NK1 and SS1 transfected cells was significantly smaller (P<0.0001) varying from 37 to 57%. The blockage of cell migration was more dramatic with the higher concentration of siRNAs. Experiments were repeated 3 times yielding similar results.

Example 5

Reduction of Inflammatory Response and Fibrosis in a Mouse Model

A conjunctival scarring mouse model was generated by injecting phosphate buffered saline (PBS) and latex beads into subconjunctival space. Inflammation response, as judged by the number of inflammatory cells in tissue sections, was more severe on post-injection day 2 compared to those obtained from eyes injected with PBS alone. The inflammatory response observed on day 2 subsided on days 4 and 7.

NK1, SS1, and scrambled siRNAs were introduced into mouse eyes together with phosphate buffered saline (PBS) and latex beads in a double masked manner. One eye of each mouse was treated with NK1 or SS1, and the contralateral eye was treated with the scrambled RNA. Eyes in other mice were either left untreated or injected with PBS and latex beads alone to serve as controls. Two days following the injection, numerous inflammatory cells were observed underneath the conjuctival epithelium in the scrambled RNA-treated and PBS/beads-injected control eyes. The inflammatory cells were less in NK1 and SS1-treated eyes.

On post-injection days 7 and 14, the number of inflammatory cells was reduced in all treated or injected eyes. The subconjunctival space in the scrambled RNA-treated and PBS/beads-injected control eyes was filled with fibroblasts. The density of conjunctival fibroblasts was higher than that seen in eyes treated with NK1 or SS1. Picrocirius red staining to demonstrate collagen deposition further showed that the fibrotic response on day 14 was repressed by NK1 and SS1 siRNAs.

Example 6

Inhibition of TGFβRII using siRNA on Endothelial Cells

Human umbical vein endothelial cells (HUVEC) were plated at 3×10-5 cells/well and allowed to grow into confluent monolayers. The following day, the cells were treated with TransIT-TKO reagent only (negative control), scrambled siRNA oligonucleotides, NK1 siRNA oligonucleotides and SS1 siRNA oligonucleotides, all in TransIT-TKO reagent. 200 nM concentrations of the oligonucleotides was used, however, greater or lesser concentrations may be used. The cellular uptake of the oligonucleotides was demonstrated by fluorescence microscopy using the Cy3-labeled luciferase. Images were taken 48 hours post RNAi treatment.

Immunofluorescence analyses showed that TGFβRII was distributed diffusely in the cytoplasm of untreated control corneal fibroblasts (FIG. 4a). In the presence of NK1 and SS1 siRNAs, the TGFβRII staining intensity was dramatically reduced (FIG. 4c and d; respectively). These results are consistent with the experiments carried out in corneal fibroblasts described in Example 2. Cells treated with scrambled siRNA (FIG. 4b) showed a similar intensity and pattern as the untreated control cells, demonstrating the specificity of NK1 and SS1 effects.

What is claimed is:

1. A siRNA molecule that reduces expression of the TGFβ type II receptor, wherein the strands of the siRNA molecule are 19-25 base pairs in length and the siRNA molecule
   (a) consists of a nucleic acid of SEQ ID NO: 5 and a nucleic acid of SEQ ID NO: 6;
   (b) consists of a nucleic acid of SEQ ID NO: 7 and a nucleic acid of SEQ ID NO: 8; or
   (c) binds to a target sequence selected from the group of SEQ ID NO: 3 and SEQ ID NO: 49.

2. A siRNA molecule of claim 1, wherein the molecule has a guanine-cytosine content ranging from 40% to 50% and does not have four identical consecutive bases.

3. A composition comprising the siRNA molecule of claim 1 and a pharmaceutically acceptable carrier.

4. The composition of claim 3, wherein the composition further comprises an additional wound healing agent.

5. A method for promoting wound healing in a mammal comprising administering a therapeutically effective amount of the composition of claim 3 to a mammal in need thereof.

6. A method for promoting wound healing in a mammal comprising administering a therapeutically effective amount of the composition of claim 4 to a mammal in need thereof.

7. A method for inhibiting fibrosis in a mammal comprising administering a therapeutically effective amount of the composition of claim 3 to a mammal in need thereof.

8. A method for inhibiting fibrosis in a mammal comprising administering a therapeutically effective amount of the composition of claim 4 to a mammal in need thereof.

9. A method for inhibiting angiogenesis in a mammal comprising administering a therapeutically effective amount of the composition of claim 3 to a mammal in need thereof.

10. A method for inhibiting angiogenesis in a mammal comprising administering a therapeutically effective amount of the composition of claim 4 to a mammal in need thereof.

11. A method of preventing glaucoma or restenosis in a mammal comprising administering to said mammal a composition of claim 3.

12. A method of preventing or treating scarring in a mammal comprising administering to said mammal a composition of claim 3.

13. The method of claim 12, wherein said scarring is coronary vessel scarring.

* * * * *